United States Patent
Barbut et al.

(10) Patent No.: US 6,589,264 B1
(45) Date of Patent: *Jul. 8, 2003

(54) AORTIC OCCLUDER WITH ASSOCIATED FILTER AND METHODS OF USE DURING CARDIAC SURGERY

(75) Inventors: Denise Barbut, New York, NY (US); Giovanni Pastrone, Los Gatos, CA (US); Tracy D. Maahs, Redwood City, CA (US); Ross S. Tsugita, Mountain View, CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/478,818

(22) Filed: Jan. 7, 2000

Related U.S. Application Data

(63) Continuation of application No. 09/008,647, filed on Jan. 16, 1998, now Pat. No. 6,090,097, which is a continuation of application No. 08/854,806, filed on May 12, 1997, now Pat. No. 6,231,544, which is a continuation-in-part of application No. 08/645,762, filed on May 14, 1996, now abandoned.

(51) Int. Cl.[7] .................................... A61M 29/00

(52) U.S. Cl. .............. 606/200; 604/96.01; 604/101.04

(58) Field of Search ................. 604/96.01, 104, 604/915, 101.04; 606/108, 113–114, 127, 128, 191, 192–194, 200, 159; 600/462, 468–470

(56) References Cited

U.S. PATENT DOCUMENTS

| | | | | |
|---|---|---|---|---|
| 4,728,319 A | * | 3/1988 | Masch | 600/585 |
| 4,737,142 A | * | 4/1988 | Heckele | 600/108 |
| 4,793,348 A | * | 12/1988 | Palmaz | 606/1 |
| 4,873,978 A | | 10/1989 | Ginsburg | 128/345 |
| 4,998,539 A | * | 3/1991 | Delsanti | 128/898 |
| 5,053,008 A | * | 10/1991 | Bajaj | 604/104 |

(List continued on next page.)

FOREIGN PATENT DOCUMENTS

| | | |
|---|---|---|
| BR | 9301980 | 10/1993 |
| DE | 3417738 A1 | 11/1985 |
| EP | 0218275 | 4/1987 |
| FR | 2567405 | 7/1984 |
| WO | 9515192 | 6/1995 |
| WO | 9516176 | 6/1995 |

OTHER PUBLICATIONS

Barbut et al., "Cerebral Emboli Detected During Bypass Surger Are Associated With Clamp Removal," *Stroke* 25(12):2398–2402 (1994).

Barbut et al., "Comparison of Transcranial Doppler Ultrasonography and Transesophagel Echocardiography to Monitor Emboli During Coronary Artery Bypass Surgery," *Stroke* 27(1):87–90 (1996).

(List continued on next page.)

*Primary Examiner*—Brian L. Casler
*Assistant Examiner*—LoAn H. Thanh
(74) *Attorney, Agent, or Firm*—O'Melveny & Myers LLP

(57) ABSTRACT

A balloon arterial cannula and methods for filtering blood. The devices generally include a mesh for filtering blood flowing within a blood vessel, particularly within an artery such as the aorta, a structure adapted to open and close the mesh within the blood vessel, a means to actuate the structure, and a balloon occluder which typically includes a flexible material enclosing a chamber. The methods generally include the steps of introducing a mesh into a blood vessel to capture embolic material, adjusting the mesh, if necessary, during the course of filtration, inflating the balloon occluder to occlude the vessel upstream of the mesh, and thereafter deflating the balloon occluder and removing the mesh and the captured foreign matter from the blood vessel. Additionally, visualization techniques are used to ensure effective filtration.

17 Claims, 26 Drawing Sheets

U.S. PATENT DOCUMENTS

| | | | | |
|---|---|---|---|---|
| 5,102,415 A | * | 4/1992 | Guenther et al. | 604/103.05 |
| 5,226,427 A | | 7/1993 | Buckberg et al. | 604/170 |
| 5,254,097 A | | 10/1993 | Schock et al. | 604/167 |
| 5,290,231 A | | 3/1994 | Marcadis et al. | 604/96 |
| 5,312,344 A | | 5/1994 | Grinfeld et al. | 604/101 |
| 5,330,451 A | | 7/1994 | Gabbay | 604/284 |
| 5,395,330 A | | 3/1995 | Marcadis et al. | 604/96 |
| 5,425,708 A | | 6/1995 | Nasu | 604/96 |
| 5,462,529 A | * | 10/1995 | Simpson et al. | 604/101.04 |
| 5,478,309 A | | 12/1995 | Sweezer et al. | 604/102 |
| 5,499,996 A | | 3/1996 | Hill | 606/201 |
| 5,505,698 A | | 4/1996 | Booth et al. | 604/96 |
| 5,522,838 A | | 6/1996 | Hill | 606/201 |
| 5,549,626 A | * | 8/1996 | Miller et al. | 606/191 |
| 5,653,690 A | | 8/1997 | Booth et al. | 604/96 |
| 5,695,519 A | * | 12/1997 | Sumners et al. | 606/200 |
| 5,707,358 A | | 1/1998 | Wright | 604/96 |
| 5,766,151 A | | 6/1998 | Valley et al. | 604/194 |
| 5,820,593 A | | 10/1998 | Safar et al. | 604/96 |
| 5,827,324 A | * | 10/1998 | Cassell et al. | 604/22 |
| 5,876,367 A | * | 3/1999 | Kaganov et al. | 604/8 |
| 5,928,192 A | | 7/1999 | Maahs | 604/96 |
| 5,941,896 A | * | 8/1999 | Kerr | 606/192 |
| 5,954,745 A | * | 9/1999 | Gertler et al. | 606/159 |
| 6,090,097 A | * | 7/2000 | Barbut et al. | 604/506 |
| 6,179,859 B1 | * | 1/2001 | Bates et al. | 606/114 |
| 6,231,544 B1 | * | 5/2001 | Tsugita et al. | 604/104 |

OTHER PUBLICATIONS daSilva et al., "Postinfarction ventricular septal defect," *J.Thorac. Cardiovasc. Surg.* 97:86–89 (1989).

daSilva et al., "Heart–lung transplantation. Initial clinical experience," *Arquivos Brasileiros de Cardiologia* 57(2):103–108 (1991) Abstract Only.

daSilva et al., "The Heart–lung transplant. Initial clinical experience," *Revista Portuguese de Cardiologia* 12(1):9, 51–5 (1993) Abstract Only.

daSilva et al., "Heteroptopic heart transplantation: A direct pulmonary artery anastomosis technique," *The Journal of Thoracic and Cardiovascular Surgery* 180(4):795 (1994).

* cited by examiner

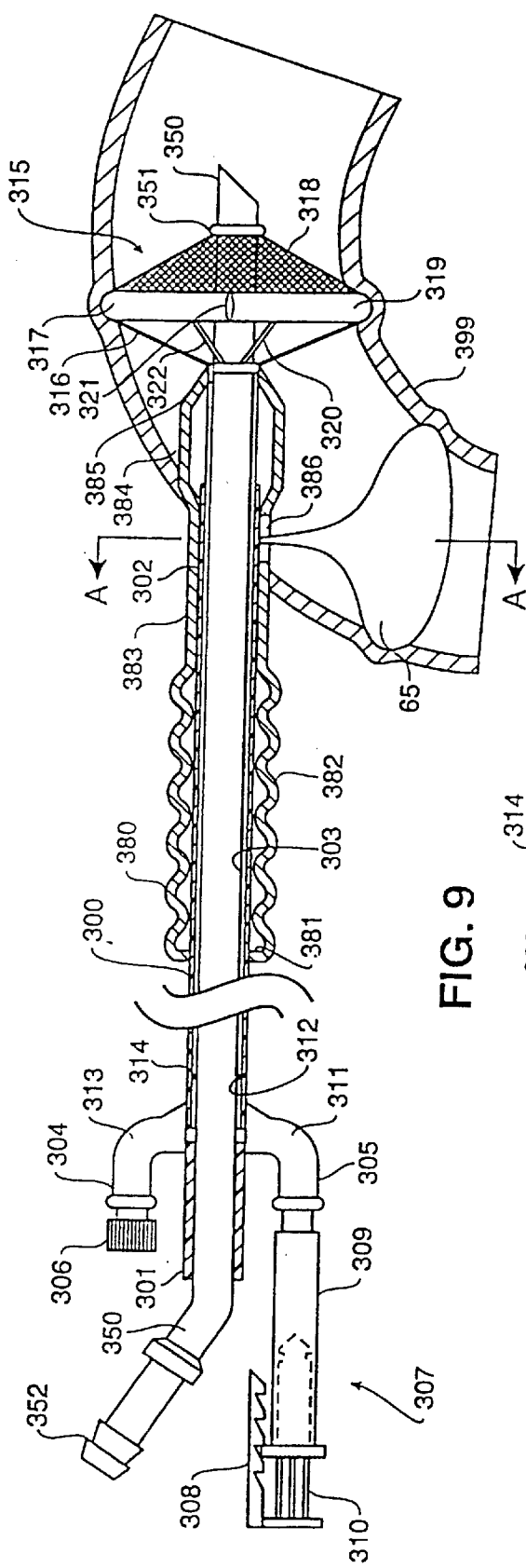
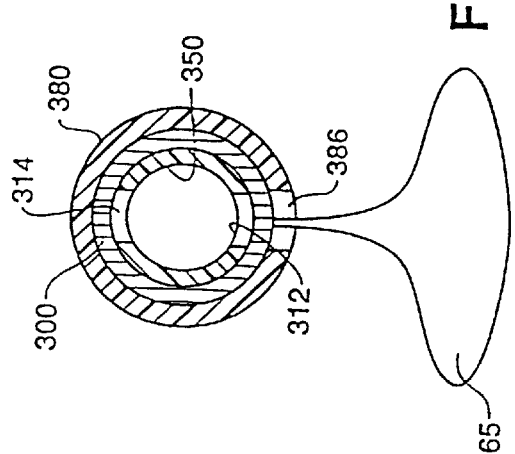
FIG. 9
FIG. 9A

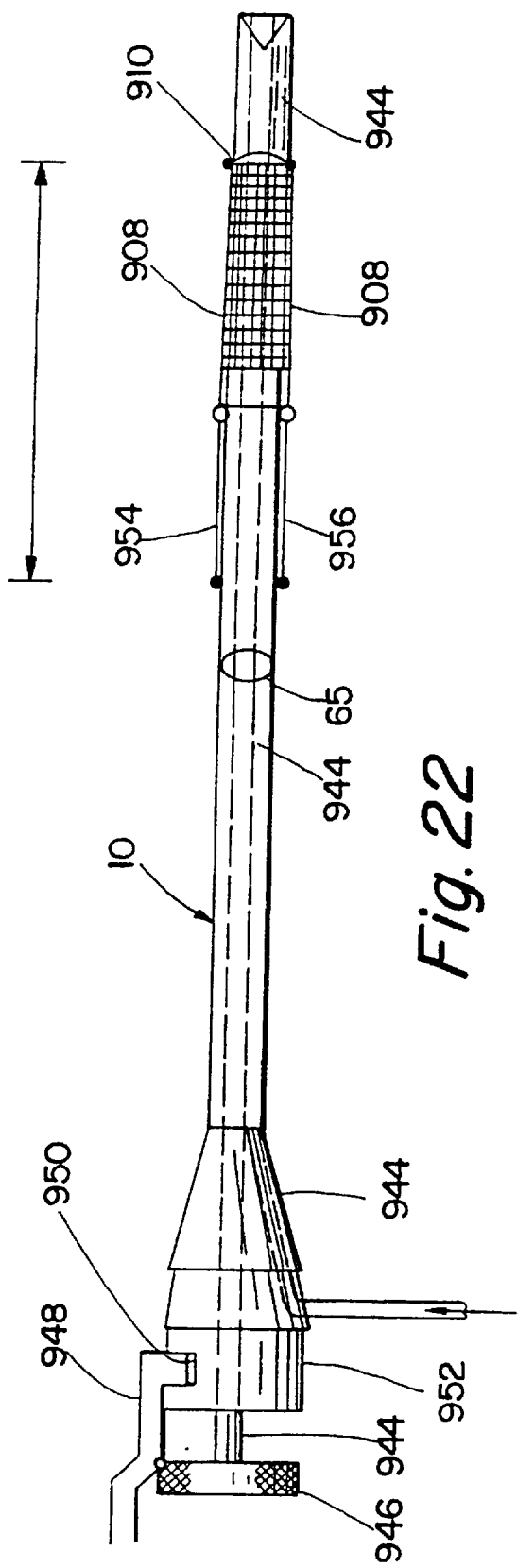
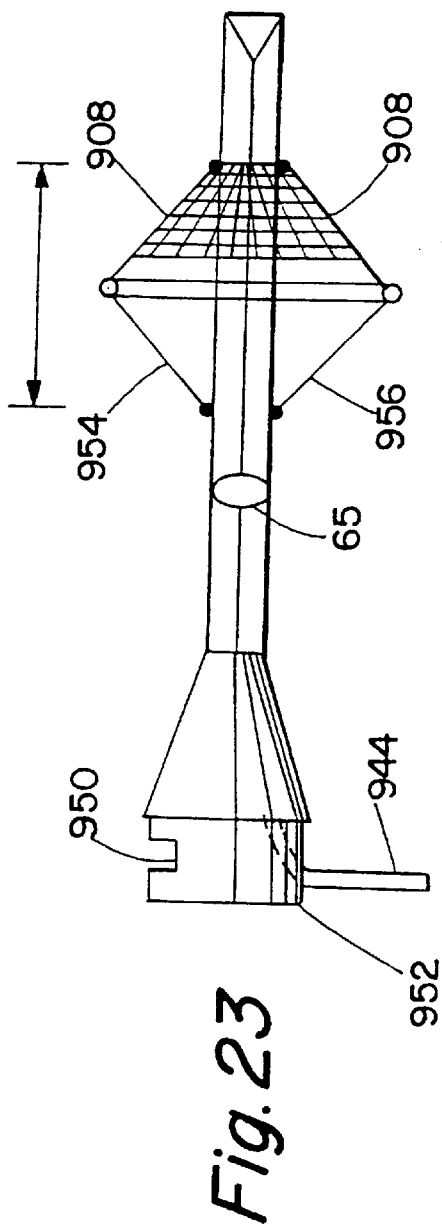
Fig. 22
Fig. 23

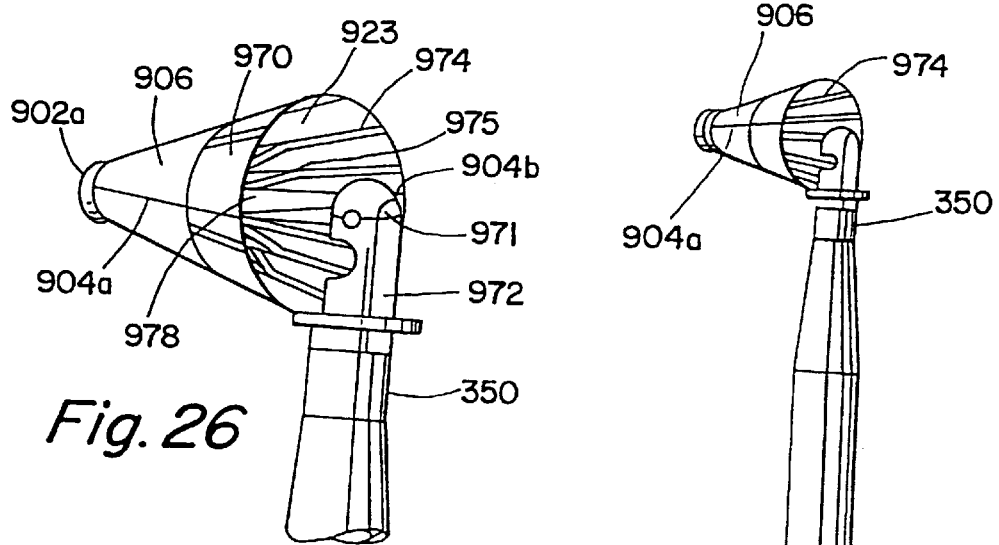
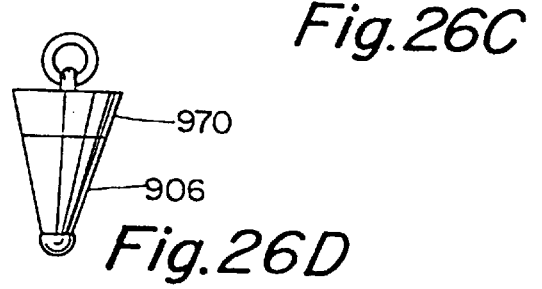
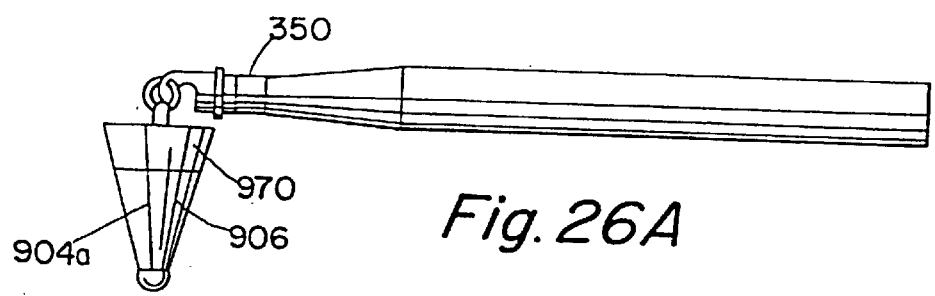
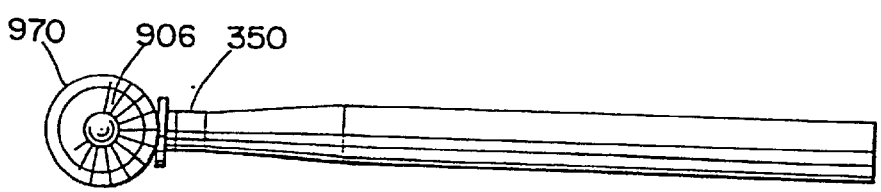

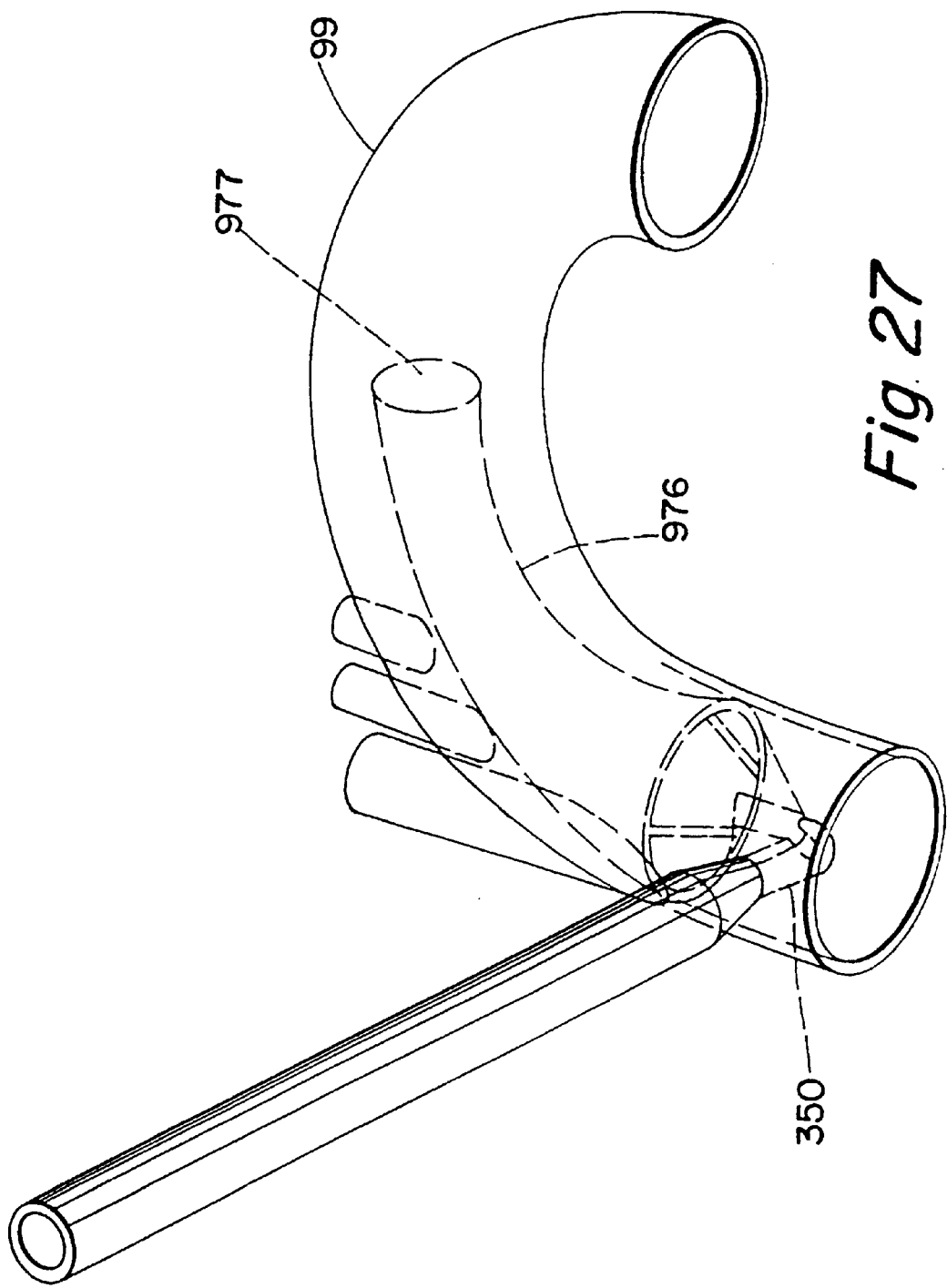

AORTIC OCCLUDER WITH ASSOCIATED FILTER AND METHODS OF USE DURING CARDIAC SURGERY

This is a continuation of U.S. application Ser. No. 09/008,647, filed Jan. 16, 1998, now U.S. Pat. No. 6,090, 097, which is a continuation of U.S. application Ser. No. 08/854,806, filed May 12, 1997, now U.S. Pat. No. 6,231, 544, which is a continuation-in-part of U.S. application Ser. No. 08/645,762, filed May 14, 1996, now abandoned. The contents of each of the above patents and applications are expressly incorporated herein by reference in their entirety.

FIELD OF THE INVENTION

The present invention relates generally to blood filter devices having an associated balloon occluder for temporary placement in a blood vessel, and more particularly to a cannula device, having an associated blood filter and balloon occluder, for placement in a blood vessel to carry blood to an artery from a bypass-oxygenator system and to capture embolic material in the vessel. The invention also relates to catheters having a balloon occluder and associated filter to capture embolic material. More particularly, the invention relates to a blood filter device to be placed in the aorta during cardiac surgery, the device further having a balloon occluder which, when deployed, reduces or eliminates the need for aortic cross-clamping. The present invention also relates to methods for temporarily filtering blood to capture and remove embolic material, and to methods for protecting a patient from embolization which may be caused by the balloon occluder having dislodged atheromatous material from the artery.

BACKGROUND OF THE INVENTION

Currently, the most common method of temporarily occluding the ascending aorta during open heart surgery utilizes a mechanical cross clamp. Once the chest cavity has been opened, access to the heart and to the adjacent vessels is provided. The ascending aorta is partially dissected from the surrounding tissue and exposed. Arterial and venous cannulas are inserted and sutured into place. The cannulas are connected to the cardiopulmonary bypass machine, and bypass blood oxygenation is established.

At this point, the heart must be arrested and isolated from the rest of the circulatory system. A mechanical cross clamp is positioned between cardioplegia cannula and the aortic cannula and actuated. The aorta is completely collapsed at the clamp site, thus stopping flow of blood between the coronary arteries and the innominate artery the oxygenated bypass blood is shunted around the heart. Once the vessel occlusion has been completed, cardioplegia solution is introduced through the cardioplegia cannula to arrest the heart. The surgeon may now proceed with the desired operation.

Other less common means of occluding the aorta include percutaneous balloon catheter occlusion, direct aortic balloon catheter (Foley) occlusion, aortic balloon occluder cannula, and an inflating diaphragm occluder (Hill— occlusion trocar). The percutaneous balloon catheter is inserted typically from the femoral artery feed through the descending aorta, across the aortic arch into position in the ascending aorta. Once in the ascending aorta, the balloon occluder is inflated and flow stopped.

As a simple replacement for the mechanical cross clamp, a Foley catheter may be placed through an additional incision site near the standard cross clamp site. Once inserted, the Foley catheter balloon is inflated and flow is stopped. Similarly, an aortic balloon occluder cannula is placed directly into the aorta. This occluder cannula replaces the standard aortic cannula by delivering the CPB blood back to the arterial circulatory system. The occluder balloon is located on the cannula proximal to CPB blood exit port on the cannula. It may also replace the need for a cardioplegia cannula with an additional infusion port proximal to the occluder balloon. The occlusion trocar is described to offer similar features as the aortic balloon occluder cannula and would be used in place of the standard aortic cannula. However, it relies on an inflatable diaphragm to occlude the vessel.

The use of a balloon to occlude an artery has been disclosed by Gabbay, U.S. Pat. No. 5,330,451 (this and all other references cited herein are expressly incorporated by reference as if fully set forth in their entirety herein). The Gabbay device included a perfusion cannula having a proximal balloon occluder and a distal intra-aortic balloon to divert blood to the carotid arteries. The Gabbay perfusion cannula is disclosed for use during open heart surgery in order to prevent complications associated therewith.

Moreover, Peters, U.S. Pat. No. 5,433,700, discusses a method for inducing cardioplegic arrest using an arterial balloon catheter to occlude the ascending aorta. The Peters method includes the steps of maintaining systemic circulation using peripheral cardiopulmonary bypass, venting the left side of the heart, and introducing a cardioplegic agent into the coronary circulation. This procedure is said to prepare the heart for a variety of surgical procedures. Disclosures of similar endovascular occlusion catheters can be found in Machold et al., U.S. Pat. No. 5,458,574, Stevens, International Application No. PCT/US93/12323, and Stevens et al., International Application No. PCT/US94/12986.

There are a number of known devices designed to filter blood. The vast majority of these devices are designed for permanent placement in veins, in order to trap emboli destined for the lungs. For example, Kimmell, Jr., U.S. Pat. No. 3,952,747, discloses the so-called Kimray-Greenfield filter. This is a permanent filter typically placed in the vena cava comprising a plurality of convergent legs in a generally conical array, which are joined at their convergent ends to an apical hub. Each leg has a bent hook at its end to impale the internal walls of the vena cava.

Cottenceau et al., U.S. Pat. No. 5,375,612, discloses a blood filter intended for implantation in a blood vessel, typically in the vena cava. This device comprises a zig-zagged thread wound on itself and a central strainer section to retain blood clots. This strainer section comprises a meshed net and may be made from a biologically absorbable material. This device is also provided with attachment means which penetrate into the wall of the vessel.

Gunther et al., U.S. Pat. No. 5,329,942, discloses a method for filtering blood in the venous system wherein a filter is positioned within a blood vessel beyond the distal end of a catheter by a positioning means guided through the catheter. The positioning means is locked to the catheter, and the catheter is anchored to the patient. The filter takes the form of a basket and is comprised of a plurality of thin resilient wires. This filter can be repositioned within the vessel to avoid endothelialization within the vessel wall.

Similarly, Lefebvre, French Patent No. 2,567,405, discloses a blood filter for implantation by an endovenous route into the vena cava. The filter is present in the form of a cone, and the filtering means may consist of a flexible metallic grid, or a flexible synthetic or plastic grid, or a weave of synthetic filaments, or a non-degradable or possibly biodegradable textile cloth. In order to hold the filter within the vein, this device includes flexible rods which are sharpened so that they may easily penetrate into the inner wall of the vena cava.

There are various problems associated with permanent filters. For example, when a filter remains in contact with the inner wall of the vena cava for a substantial period of time, endothelialization takes place and the filter will subsequently become attached to the vena cava. This endothelialization may cause further occlusion of the vessel, thereby contributing to the problem the filter was intended to solve. Except for the Gunther device, these prior art filters do not address this problem.

A temporary venous filter device is disclosed in Bajaj, U.S. Pat. No. 5,053,008. This device treats emboli in the pulmonary artery which, despite its name, is in fact a vein. The Bajaj device is an intracardiac catheter for temporary placement in the pulmonary trunk of a patient predisposed to pulmonary embolism because of hip surgery, stroke or cerebral hemorrhage, major trauma, major abdominal or pelvic surgery, neurosurgery, neoplasm, sepsis, cardiorespiratory failure or immobilization.

The Bajaj device includes an umbrella made from meshwork which traps venous emboli before they reach the lungs. This device can also lyse emboli with a thrombolytic agent such as tissue plasminogen activator (TPA), destroy emboli with high velocity ultrasound energy, and remove emboli by vacuum suction through the lumen of the catheter. This very complex device is designed for venous filtration and is difficult to justify when good alternative treatments exist.

There are very few intravascular devices designed for arterial use. A filter that functions not only in veins, but also in arteries must address additional concerns because of the hemodynamic differences between arteries and veins. Arteries are much more flexible and elastic than veins and, in the arteries, blood flow is pulsatile with large pressure variations between systolic and diastolic flow. These pressure variations cause the artery walls to expand and contract. Blood flow rates in the arteries vary from about 1 to about 5 L/min.

Ginsburg, U.S. Pat. No. 4,873,978, discloses an arterial device. This device includes a catheter that has a strainer device at its distal end. This device is normally used in conjunction with non-surgical angioplasty treatment. This device is inserted into the vessel downstream from the treatment site and, after the treatment, the strainer is collapsed around the captured emboli, and the strainer and emboli are removed from the body. The Ginsburg device could not withstand flow rates of 5 L/min. It is designed for only small arteries and therefore could not capture emboli destined for all parts of the body. For example, it would not catch emboli going to the brain.

Ing. Walter Hengst GmbH & Co, German Patent DE 34 17 738, discloses another filter which may be used in the arteries of persons with a risk of embolism. This filter has an inherent tension which converts the filter from the collapsed to the unfolded state, or it can be unfolded by means of a folding linkage system. This folding linkage system comprises a plurality of folding arms spaced in parallel rows along the longitudinal axis of the conical filter (roughly similar to branches on a tree). The folding arms may be provided with small barbs at their projecting ends intended to penetrate the wall of the blood vessel to improve the hold of the filter within the vessel.

Moreover, da Silva, Brazil Patent Application No. PI 9301980A, discusses an arterial filter for use during certain heart operations where the left chamber of the heart is opened. The filter in this case is used to collect air bubbles in addition to formed particles such as platelet fibrin clots not removed on cleaning the surgical site.

Each of the existing methods of blocking aortic blood flow carries with it some undesired aspects. The mechanical cross clamp offers simplicity and reliably consistent operation. However, the physical clamping action on the vessel has been linked to may adverse body responses. Barbut et al. noted the majority of embolic events (release) is associated with the actuation and release of the cross clamp during coronary bypass graph surgery. The clamping action may be responsible for breaking up and freeing atherosclerotic buildup on the vessel walls. In addition, the potential for vascular damage, like aortic dissections, may also incur during the clamp application.

The percutaneous balloon catheter occluder has a distinct drawback in that it must be placed with visionary assistance. Fluoroscopy is typically used to position the device in the aorta. This added equipment is not always readily available in the surgical suite. In addition, the catheter placement up to the aorta may also create additional vascular trauma and emboli generation.

The use of a Foley catheter to occlude the aorta requires an additional incision site to place the device. This extra cut is an additional insult site and requires sutures to close. Generation of emboli and the potential of aortic dissection directly associated with just the incision may potentially outweigh the benefits of using the balloon occlusion technique.

The aortic balloon occluder cannula addresses many of the deficiencies of the previous devices. Placement is easy to visualize and no extra cuts are required. With the cardioplegia port included, this design offers a complete package while potentially reducing the number of incision sites and removing the need for the potentially traumatic cross clamp. However, this "all-in-one" design possesses several deficiencies. First, there is one inherent drawback with using a balloon to occlude a vessel. Balloons are always susceptible to failure (e.g., popping, leaking). In addition, the cannula has a limited placement region. It must be inserted sufficiently proximal to the innominate artery to allow room for occlusion balloon to seat within the vessel and not occlude or block the innominate artery. This cannula design has at least two critical functions (three with the cardioplegia port). A balloon failure means either replacing the cannula (stopping the CPB and cardioplegia), or immediately placing the cross clamp and inserting a cardioplegia cannula. Life support, occlusion, and cardioplegia depend on one device. This situation is less than optimal. The risks associated to a failure are multiplied when one device is used for more than one critical operation.

A need exists for an arterial cannula having both a balloon occluder, which reduces or eliminates the need for aortic cross-clamping, a major contributor to atheromatous embolization, and an associated filter which captures any embolic material dislodged during balloon occlusion. Existing devices are inadequate for this purpose.

SUMMARY OF THE INVENTION

The present invention relates to arterial medical devices, and particularly cannulas and catheters having an occlusion balloon and optionally a blood filter device, and to methods of using the devices during cardiac surgery. The devices of the present invention may be adapted to filter embolic material from the blood. Embolic material or foreign matter is any constituent of blood, including gaseous material and particulate matter, which may cause complications in the body if allowed to travel freely in the bloodstream. This matter includes but is not limited to atheromatous fragments, fat, platelets, fibrin, clots, or gaseous material.

In one embodiment, the device includes a blood cannula having a balloon occluder at a distal region of the blood cannula. In another embodiment, the device includes an intravascular catheter having a balloon occluder at a distal region of the catheter. The balloon occluder may consist of a flexible material surrounding a chamber which is expandable between a deflated, contracted condition and an inflated, enlarged condition. The balloon occluder may be circumferentially disposed about a distal region of the catheter or blood cannula, or may be attached to the catheter or blood cannula at a specific radial position about the distal region of the catheter or blood cannula. The balloon occluder, when in the contracted condition, is closely associated with the distal region of the catheter or blood cannula, while the balloon occluder expands upon inflation to occupy an area which may occlude blood flowing within an artery.

In another embodiment, the blood cannula or catheter will further include filtration means disposed about the distal region of the catheter or blood cannula. Several designs for blood filtration cannulas are disclosed in Barbut et al., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, and Barbut et al., U.S. Pat. No. 5,769,816, filed on Apr. 30, 1996, and Barbut et al., U.S. Pat. No. 5,989,281, filed Apr. 16, 1997, and the contents of each of these prior applications are incorporated herein by reference in their entirety. Thus, in one embodiment, the balloon aortic cannula as disclosed herein will include a filtration means having an expandable member, such as an inflation seal, disposed about the distal end of the blood cannula, which is expandable between a deflated, contracted condition and an inflated, enlarged condition. The filtration means will further include a mesh having an edge attached to the expansion means. The mesh may optionally include a second edge which is closely associated with the outer surface of the blood cannula, or the mesh may be continuous and unbroken at its distal region. The filtration means will generally be disposed about the distal end of the blood cannula and the balloon occluder at a region proximal of the mesh, so that the balloon occluder expands upon inflation to substantially occlude an artery upstream of the mesh. For those embodiments using an intravascular catheter, the balloon occluder is typically upstream of the filtration means, or with reference to the catheter, distal the filtration means.

In another embodiment, a cannula with filtration means further includes a blood flow diffuser. The blood flow diffuser may be located inside or outside of the blood cannula. In both the intra-cannula and extra-cannula diffuser embodiments, the flow diffuser can be located either proximal or distal to the filtration means. The diffuser may be similarly used for intravascular catheter embodiments of the device.

In another embodiment, a cannula with attached filtration means includes a sleeve which, when unrolled, captures the filtration means thereby closely securing the filter components against the cannula wall during insertion and retraction. The sleeve may be similarly used for intravascular catheter embodiments of the device. In another embodiment, a cannula is made of an elastomeric material which collapses along part of the cannula length so as to absorb the filtration means during cannula insertion and retraction.

In an alternate embodiment, a blood cannula includes a conduit to provide a solution, such as cardioplegia solution, to the heart side of an aortic balloon occluder while providing oxygenated blood into the arterial circulation of the systemic side of the occluder.

The methods of the present invention include protecting a patient from embolization during cardiac surgery by using a balloon aortic cannula as described above or other intravascular or intra-arterial procedure resulting in distal embolization. The distal end of the arterial cannula is inserted into a patient's aorta while the filtration and expansion means is in the contracted condition. The expansion means, including associated mesh, is inflated to expand and thereby achieve contact with the inner wall of the artery, preferably the aorta. Once the filtration means are in place and deployed, the balloon occluder is activated by inflating to occlude the artery, preferably the aorta, in a region upstream of the mesh. In other embodiments, the balloon occluder may be inflated before the expansion means is inflated. During balloon occlusion, certain embolic material may be dislodged from the artery, and thereafter captured by the deployed filtration system. The cannula is used to supply blood to the aorta from a bypass-oxygenator machine. A surgical procedure may then be performed on the heart, aorta, or vasculature upstream of the deployed filtration system. During this procedure, further embolic material may be dislodged and enter the circulation, and thereafter be captured by the deployed filtration mesh. After the surgery is performed, the balloon occluder is deflated, and further embolic material may be dislodged and captured by the filtration system. The expansion means of the filtration system is then contracted by deflating to resume a small shape, and the arterial cannula with captured embolic material is removed from the aorta.

In a preferred method, balloon occlusion occurs, and blood is filtered during cardiac surgery, in particular during cardiac bypass surgery, to protect a patient from embolization. In this method, the mesh is positioned in the aorta where it filters blood before it reaches the carotid arteries, brachiocephalic trunk, and left subclavian artery.

The present invention was developed, in part, in view of a recognition of the occurrence of embolization during cardiac surgery. Emboli are frequently detected in cardiac surgery patients and have been found to account for neurologic, cardiac and other systemic complications. Specifically, embolization appears to contribute significantly to problems such as strokes, lengthy hospital stays and, in some cases, death. Of the patients undergoing cardiac surgery, 5–10% experience strokes and 30% become cognitively impaired. In addition, it has been recognized that embolization is often the result of procedures performed on blood vessels such as incising, clamping, and cannulation, wherein mechanical or other force is applied to the vessel. See, for example, Barbut et al., "Cerebral Emboli Detected During Bypass Surgery Are Associated With Clamp Removal," Stroke 25(12):2398–2402 (1994), which is incorporated herein by reference in its entirety. These procedures are commonly performed in many different types of surgery including cardiac surgery, coronary artery surgery including coronary artery bypass graft surgery, aneurysm repair surgery, angioplasty, atherectomy, and endarterectomy, including carotid endarterectomy. It has also been recognized that reintroducing blood into blood vessels with a cannula or catheter during these procedures can dislodge plaque and other emboli-creating materials as a result of blood impinging upon the vessel wall at high velocities. See, for example, Cosgrove et. al., Low Velocity Aortic Cannula, U.S. Pat. No. 5,354,288.

Finally, it has been found that the occurrence of embolization is more likely in certain types of patients. For example, embolization occurs more frequently in elderly patients and in those patients who have atheromatosis. In fact, atheromatous embolization, which is related to severity of aortic atheromatosis, is the single most important contributing factor to perioperative neurologic morbidity in patients undergoing cardiac surgery.

Embolic material, which has been detected at 2.88 mm in diameter, will generally range from 0.02 mm (20 µm) to 5 mm, and consists predominantly of atheromatous fragments dislodged from the aortic wall and air bubbles introduced during dissection, but also includes platelet aggregates which form during cardiac surgery. See Barbut et al., "Determination of Embolic Size and Volume of Embolization During Coronary Artery Bypass Surgery Using Transesophageal Echocardiography," J. Cardiothoracic Anesthesia (1996). These emboli enter either the cerebral circulation or systemic arterial system. Those entering the cerebral circulation obstruct small arteries and lead to macroscopic or microscopic cerebral infarction, with ensuing neurocognitive dysfunction. Systemic emboli similarly cause infarction, leading to cardiac, renal, mesenteric, and other ischemic complications. See Barbut et al., "Aortic Atheromatosis And Risks of Cerebral Embolization," Journal of Cardiothoracic and Vascular Anesthesia 10(1):24–30 (1996), which is incorporated herein by reference in its entirety.

Emboli entering the cerebral circulation during coronary artery bypass surgery have been detected with transcranial Doppler ultrasonography (TCD). TCD is a standard visualization technique used for monitoring emboli in the cerebral circulation. To detect emboli using TCD, the middle cerebral artery of a bypass patient is continuously monitored from aortic cannulation to bypass discontinuation using a 2 MHZ pulsed-wave TCD probe (Medasonics-CDS) placed on the patient's temple at a depth of 4.5 to 6.0 cm. The number of emboli is determined by counting the number of embolic signals, which are high-amplitude, unidirectional, transient signals, lasting less than 0.1 second in duration and associated with a characteristic chirping sound.

TCD is useful in analyzing the relationship between embolization and procedures performed on blood vessels. For example, the timing of embolic signals detected by TCD have been recorded along with the timing of procedures performed during open or closed cardiac surgical procedures. One of these procedures is cross-clamping of the aorta to temporarily block the flow of blood back into the heart. It has been found that flurries of emboli are frequently detected after aortic clamping and clamp release. During the placement and removal for the clamps, atheromatous material along the aortic wall apparently becomes detached and finds its way to the brain and other parts of the body. Similarly, flurries of emboli are also detected during aortic cannulation and inception and termination of bypass.

Transesophageal echocardiography (TEE), another standard visualization technique known in the art, is significant in the detection of conditions which may predispose a patient to embolization. TEE is an invasive technique, which has been used, with either biplanar and multiplanar probes, to visualize segments of the aorta, to ascertain the presence of atheroma. This technique permits physicians to visualize the aortic wall in great detail and to quantify atheromatous aortic plaque according to thickness, degree of intraluminal protrusion and presence or absence of mobile components, as well as visualize emboli within the vascular lumen. See, for example, Barbut et al., "Comparison of Transcranial Doppler and Transesophageal Echocardiography to Monitor Emboli During Coronary Bypass Surgery," Stroke 27(1): 87–90 (1996) and Yao, Barbut et al., "Detection of Aortic Emboli By Transesophageal Echocardiography During Coronary Artery Bypass Surgery," Journal of Cardiothoracic Anesthesia 10(3):314–317 (May 1996), and Anesthesiology 83(3A):A126 (1995) which are incorporated herein by reference in their entirety. Through TEE, one may also determine which segments of a vessel wall contain the most plaque. For example, in patients with aortic atheromatous disease, mobile plaque has been found to be the least common in the ascending aorta, much more common in the distal arch and most frequent in the descending segment. Furthermore, TEE-detected aortic plaque is unequivocally associated with stroke. Plaque of all thickness is associated with stroke but the association is strongest for plaques over 4 mm in thickness. See Amarenco et al., "Atherosclerotic disease of the aortic arch and the risk of ischemic stroke," New England Journal of Medicine 331:1474–1479 (1994).

Another visualization technique, intravascular ultrasound, is also useful in evaluating the condition of a patient's blood vessel. Unlike the other techniques mentioned, intravascular ultrasound visualizes the blood vessel from its inside. Thus, for example, it may be useful for visualizing the ascending aorta overcoming deficiencies of the other techniques. In one aspect of the invention, it is contemplated that intravascular ultrasound is useful in conjunction with devices disclosed herein. In this way, the device and visualizing means may be introduced into the vessel by means of a single catheter.

Through visualization techniques such as TEE epicardial aortic ultrasonography and intravascular ultrasound, it is possible to identify the patients with plaque and to determine appropriate regions of a patient's vessel on which to perform certain procedures. For example, during cardiac surgery, in particular, coronary artery bypass surgery, positioning a probe to view the aortic arch allows monitoring of all sources of emboli in this procedure, including air introduced during aortic cannulation, air in the bypass equipment, platelet emboli formed by turbulence in the system and atheromatous emboli from the aortic wall. Visualization techniques may be used in conjunction with a blood filter device to filter blood effectively. For example, through use of a visualization technique, a user may adjust the position of a blood filter device, and the degree of actuation of that device as well as assessing the efficacy of the device by determining whether foreign matter has bypassed the device.

It is an object of the present invention to eliminate or reduce the problems that have been recognized as relating to embolization. The present invention is intended to capture and remove emboli in a variety of situations, and to reduce the number of emboli by obviating the need for cross clamping. For example, in accordance with one aspect of the invention, blood may be filtered in a patient during procedures which affect blood vessels of the patient. The present invention is particularly suited for temporary filtration of blood in an artery of a patient to capture embolic debris. This in turn will eliminate or reduce neurologic, cognitive, and cardiac complications helping to reduce length of hospital stay. In accordance with another aspect of the invention, blood may be filtered temporarily in a patient who has been identified as being at risk for embolization.

As for the devices, one object is to provide simple, safe and reliable devices that are easy to manufacture and use. A further object is to provide devices that may be used in any blood vessel. Yet another object is to provide devices that will improve surgery by lessening complications, decreasing the length of patients' hospital stays and lowering costs associated with the surgery. See Barbut et al., "Intraoperative Embolization Affects Neurologic and Cardiac Outcome and Length of Hospital Stay in Patients Undergoing Coronary Bypass Surgery," Stroke (1996).

nula and catheter procedures by coordinating filtration and blood flow diffusion techniques in a single device. Another object is to provide a method of inserting or retrieving a cannula or catheter with attached filtering means from a vessel while minimizing the device's profile and diameter.

Thus, we disclose herein each of the individual designs listed below which are grouped into three categories.

| DESIGN | | ADVANTAGE | |
|---|---|---|---|
| Aortic cannula based: | | | |
| Mechanical Occluder | | 1. | No additional holes/incisions required. |
| 1. | Basket with dam | 2. | Reliable actuation mechanism. |
| 2. | Basket with dam and inflatable seal | 3. | Non-migrating positioning seal. Stability. |
| | | 4. | Rugged design; will not burst (except #2) |
| 3. | Basket with removable dam | 5. | No fluoroscopy required. |
| | | 6. | Potentially less traumatic to vessel than mechanical cross clamps. |
| 4. | Expandable wire basket | | |
| Inflatable Occluder | | 1. | No additional holes/incisions required (except #4). |
| 1. | Balloon with adhesive seal | | |
| | | 2. | Conforming seal; adjusts to any shape. |
| 2. | Self-inflating balloon | 3. | Potentially less traumatic to vessel than mechanical cross clamps. |
| 3. | Self-inflating balloon on a collapsible cannula | | |
| | | 4. | Adhesive seal reduces potential for leakage and adds to occluder stability. |
| 4. | Balloon catheter | | |
| 5. | Balloon catheter with aortic cannula introducer | 5. | Self-inflating units are self-sealing occluder. |
| | | 6. | Catheter systems decoupled from cannula. Units can be inserted to desired location independent of cannula position. |
| 6. | Balloon catheter with aortic cannula introducer and guide | | |
| | | 7. | No fluoroscopy required. |
| Cardioplegia cannula based: | | | |
| Inflatable Occluder | | 1. | Same as other inflatable occluders (listed above). |
| 1. | Balloon cannula | | |
| 2. | Balloon catheter through cannula | 2. | Occlusion device separate from aortic cannula. Reduces complexity of critical device. |
| 3. | Port access occluder | 3. | Port access design does not require partial or full sternotomy. |
| | | 4. | No fluoroscopy required. |

The devices disclosed herein have the following characteristics: can withstand high arterial blood flow rates for an extended time; include a mesh that is porous enough to allow adequate blood flow in a blood vessel while capturing mobile emboli; can be used with or without imaging equipment; remove the captured emboli when the operation has ended; will not dislodge mobile plaque; and can be used in men, women, and children of varying sizes.

As for methods of use, an object is to provide temporary occlusion and filtration in any blood vessel and more particularly in any artery. A further object is to provide a method for temporarily filtering blood in an aorta of a patient before the blood reaches the carotid arteries and the distal aorta. A further object is to provide a method for filtering blood in patients who have been identified as being at risk for embolization. Yet a further object is to provide a method to be carried out in conjunction with a blood filter device and visualization technique that will assist a user in determining appropriate sites of filtration. This visualization technique also may assist the user in adjusting the blood filter device to ensure effective filtration. Yet a further object is to provide a method for filtering blood during surgery only when filtration is necessary. Yet another object is to provide a method for eliminating or minimizing embolization resulting from a procedure on a patient's blood vessel by using a visualization technique to determine an appropriate site to perform the procedure.

Another object is to provide a method for minimizing incidence of thromboatheroembolisms resulting from can-

BRIEF DESCRIPTION OF DRAWINGS

Reference is next made to a brief description of the drawings, which are intended to illustrate balloon aortic cannula and catheter devices for use herein. The drawings and detailed description which follow are intended to be merely illustrative and are not intended to limit the scope of the invention as set forth in the appended claims.

FIG. 9 is a longitudinal view of a balloon aortic cannula according to another embodiment;

FIG. 9A is a cross-sectional view through section line A—A of the device depicted in FIG. 9;

FIG. 22 is a longitudinal view of a balloon aortic elastic cannula wherein the cannula's outer diameter and filter profile are reduced by introduction of a stylet in the cannula's central lumen.

FIG. 23 is a longitudinal view of a balloon aortic elastic cannula wherein the elastic cannula is in a relaxed state.

FIGS. 26 and 26c depict a cannula wherein the filter has an elastomeric compliant edge which conforms to vessel irregularities.

FIGS. 26a, 26b and 26d show other views of the cannula depicted in FIG. 26c.

FIG. 27 shows a cannula having an open-ended sleeve disposed within the aorta.

DETAILED DESCRIPTION

Figure 1:
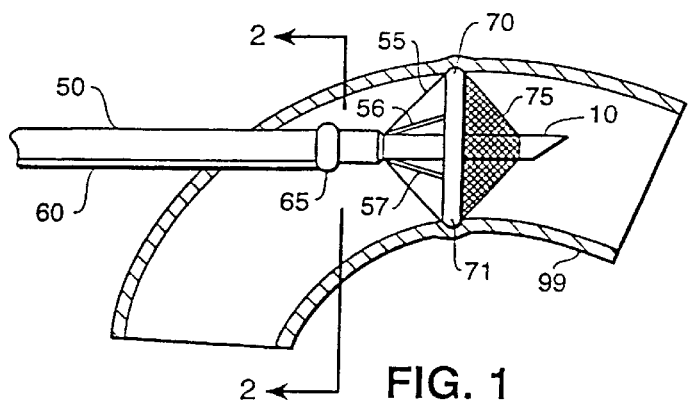
FIG. 1 is a longitudinal view of a balloon aortic cannula according to one embodiment having the filter deployed and the balloon occluder in the contracted condition.

To filter blood effectively, i.e., to capture embolic material, without unduly disrupting blood flow, the mesh must have the appropriate physical characteristics, including area ($A_M$), thread diameter ($D_T$), and pore size ($S_P$). In the aorta, the mesh 40 must permit flow rates as high as 3 L/min or more, more preferably 3.5 L/min or more, more preferably 4 L/min or more, more preferably 4.5 L/min or more, more preferably 5 L/min or more preferably 5.5 L/min or more, and most preferably 6 L/min or more at pre-filter pressures (proximal to the mesh) of around 120 mm Hg or less.

In order to capture as many particles as possible, mesh with the appropriate pore size must be chosen. The dimensions of the particles to be captured is an important factor in this choice. In the aorta during cardiac surgery, for example, individual particle diameter has been found to range from 0.27 mm to 2.88 mm, with a mean diameter of 0.85 mm, and individual particle volume has been found to range from 0.01 $mm^3$ to 12.45 $mm^3$, with a mean particle volume of 0.32 mm³. Approximately 27 percent of the particles have been found to measure 0.6 mm or less in diameter. During cardiac bypass surgery in particular, the total aortic embolic load has been found to range from 0.57 cc to 11.2 cc, with a mean of 3.7 cc, and an estimated cerebral embolic load has been found to range from 60 mm³ to 510 mm³, with a mean of 276 mm³.

By way of example, when a device as disclosed herein is intended for use in the aorta, the area of the mesh required for the device is calculated in the following manner. First, the number of pores $N_P$ in the mesh is calculated as a function of thread diameter, pore size, flow rate, upstream pressure and downstream pressure. This is done using Bernoulli's equation for flow in a tube with an obstruction:

$$\frac{P_1}{\rho * g} + \frac{V_1^2}{2 * g} = \frac{P_2}{\rho * g} + \frac{V_2^2}{2 * g} * A$$

In this equation, P is pressure, ρ is density of the fluid, g is the gravity constant (9.8 m/s²), V is velocity, K represents the loss constants, and f is the friction factor. The numbers 1 and 2 denote conditions upstream and downstream, respectively, of the filter.

The following values are chosen to simulate conditions within the aorta:
$P_1$=120 mm Hg;
$P_2$=80 mm Hg;
$K_{entry}$=0.5;
$K_{exit}$=1.0;
$K=K_{entry}+K_{exit}$; and
$[D_T/S_P]_{Equiv}$ is 30.
Assuming laminar flow out of the mesh filter, f is given as $$64/Re$$

where Re is the Reynold's number and the Reynold's number is given by the following equation:

$$Re = \frac{(\rho * Q * S_P)}{(\mu * N_P * A_h)}$$

where μ is the kinematic viscosity of the fluid and $A_h$ is the area of one hole in the mesh given by $S_p*S_p$.

Conservation of the volume dictates the following equation:

$$N_P * V_2 * A_h = Q \text{ OR } V_2 = \frac{Q}{(N_P * A_h)}$$

where Q is the flow rate of the blood. In addition, $V_1$ is given by:

$$V_1 = \frac{Q}{A_{vessel}}$$

where $A_{vessel}$ is the cross-sectional area of the vessel. Substitution and manipulation of the above equations yields $N_P$.

Next, the area of the mesh is calculated as a function of the number of pores, thread diameter and pore size using the following equation:

$$A_M = N_P * (D_T + S_P)^2$$

In an embodiment of the device 10 that is to be used in the aorta, mesh with dimensions within the following ranges is desirable: mesh area is 3–10 in², more preferably 4–9 in², more preferably 5–8 in² more preferably 6–8 in², most preferably 7–8 in²; mesh thickness is 20–280 μm, more preferably 23–240 μm, more preferably 26–200 μm, more preferably 29–160 μm, more preferably 32–120 μm, more preferably 36–90 μm, more preferably 40–60 μm; thread diameter is 10–145 μm, more preferably 12–125 μm, more preferably 14–105 μm, more preferably 16–85 μm, more preferably 20–40 μm; and pore size is 50–300 μm, more preferably 57–285 μm, more preferably 64–270 μm, more preferably 71–255 μm, more preferably 78–240 μm, more preferably 85–225 μm, more preferably 92–210 μm, more preferably 99–195 μm, more preferably 106–180 μm, more preferably 103–165 μm, more preferably 120–150 μm. In a preferred embodiment of the invention, mesh area is 3–8 in², mesh thickness is 36–90 μm, thread diameter is 16–85 μm, and pore size is 103–165 μm. In a further preferred embodiment of the invention, mesh area is 3–5 in², mesh thickness is 40–60 μm, thread diameter is 20–40 μm, and pore size is 120–150 μm.

The calculation set forth above has been made with reference to the aorta. It will be understood, however, that blood flow parameters within any vessel other than the aorta may be inserted into the equations set forth above to calculate the mesh area required for a blood filter device adapted for that vessel.

To test the mesh under conditions simulating the conditions within the body, fluid flow may be observed from a reservoir through a pipe attached to the bottom of the reservoir with the mesh placed over the mouth of the pipe through which the fluid exits the pipe. A mixture of glycerin and water may be used to simulate blood. Fluid height (h) is the length of the pipe in addition to the depth of the fluid in the reservoir, and it is given by the following equation:

$$h = \frac{P}{(\rho * g)}$$

where ρ is given by the density of the glycerin-water mixture, and g is given by the gravity constant (9.8 ms²).

Bernoulli's equation (as set forth above) may be solved in order to determine $(D_T/S_P)_{Equiv}$. $V_1$ is given by the following equation:

$$V_1 = \frac{Q}{A_1}$$

where Q is the flow rate which would be measured during testing and $A_1$ is the cross-sectional area of the pipe. $V_2$ is given by the following equation:

$$V_2 = \frac{Q}{(N * A_2)}$$

where N is the number of pores in the mesh and $A_2$ is the area of one pore. Further, $P_1$=120 mm Hg and $P_2$=0 mm Hg and $S_P$ is the diagonal length of the pore. Reynold's number (Re) is given by the following equation:

$$Re = \frac{(\rho * V_2 * D)}{\mu}$$

where ρ and μ are, respectively, the density and kinematic viscosity of the glycerin-water mixture.

Once appropriate physical characteristics are determined, suitable mesh can be found among standard meshes known in the art. For example, polyurethane meshes may be used, such as Saati and Tetko meshes. These are available in sheet form and can be easily cut and formed into a desired shape. In a preferred embodiment, the mesh is sonic welded into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids also may be used, e.g., monoclonal antibodies such as ReoPro (Centocore). The anticoagulant may be painted or sprayed onto the mesh. A chemical dip comprising the anticoagulant also may be used. Other methods known in the art for applying chemicals to mesh may be used.

In an embodiment of the devices suited for placement in the aorta, the expansion means, upon deployment, has an outer diameter of approximately 100 Fr., more preferably 105 Fr., more preferably 110 Fr., more preferably 115 Fr., more preferably 120 Fr., and most preferably 125 Fr., or greater, and an inner diameter of approximately 45 Fr. (1 Fr. =0.13 in.) when fully inflated. The dimensions of the expansion means may be adjusted in alternative embodiments adapted for use in vessels other than the aorta. Alternatively, expandable members other than a balloon also may be used with this invention. Other expandable members include the umbrella frame with a plurality of arms as described in U.S. application Ser. Nos. 08/533,137, 08/580,223, 08/584,759, U.S. Pat. No. 5,769,816, U.S. Pat. No. 5,989,281, and U.S. Pat. No. 5,911,734.

All components of this device should be composed of materials suitable for insertion into the body. Additionally, sizes of all components are determined by dimensional parameters of the vessels in which the devices are intended to be used. These parameters are known by those skilled in the art.

By way of purely illustrative example, the operational characteristics of a filter according to the invention and adapted for use in the aorta are as follows:

| | |
|---|---|
| Temperature Range | 25–39 degrees C. |
| Pressure Range | 50–150 mm Hg |
| Flow Rate | usually up to 5 L/min., can be as high as 6 L/min. |
| Duration of single use | up to approximately 5 hours |
| Average emboli trapped | 5–10,000 |
| Pressure gradient range | (100–140)/(50–90) |

Modification of the operational characteristics set forth above for use in vessels other than the aorta are readily ascertainable by those skilled in the art in view of the present disclosure. An advantage of all embodiments disclosed herein is that the blood filter will capture emboli which may result from the incision through which the blood filter is inserted. Another advantage is that both the balloon occluder and the filter means enter the vessel through the same incision created for the blood cannula, and therefore the devices and methods herein economize on incisions made in the blood vessel, often the aorta.

In addition, use of visualization techniques is also contemplated in order to determine which patients require filtration (identify risk factors), where to effectively position a blood filter device to maximize effectiveness, when to adjust the device if adjustment is necessary, when to actuate the device and appropriate regions for performing any procedures required on a patient's blood vessel.

In accordance with one aspect of the invention, a visualization technique, such as TCD, is used to determine when to actuate a blood filter device. For example, during cardiac bypass surgery, flurries of emboli are detected during aortic cannulation, inception, and termination of bypass and cross-clamping of the aorta. Therefore, a mesh may be opened within a vessel downstream of the aorta during these procedures and closed when embolization resulting from these procedures has ceased. Closing the mesh when filtration is not required helps to minimize obstruction of the blood flow.

According to another embodiment, a visualization technique is used to monitor emboli entering cerebral circulation to evaluate the effectiveness of a blood filter device in trapping emboli. Also, a visualization technique is useful to positioning a device within a vessel so that it operates at optimum efficiency. For example, a user may adjust the position of the device if TCD monitoring indicates emboli are freely entering the cerebral circulation. In addition, a user may adjust a mesh of a blood filter device to ensure that substantially all of the blood flowing in the vessel passes through the mesh.

According to yet another embodiment, a visualization technique, such as intravascular ultrasonography, TEE, and epicardial aortic ultrasonography, is used to identify those patients requiring blood filtration according to the present invention. For example, these visualization techniques may be used to identify patients who are likely to experience embolization due to the presence of mobile plaque. These techniques may be used before the patient undergoes any type of procedure which will affect a blood vessel in which mobile plaque is located.

Additionally, visualization techniques may be used to select appropriate sites on a blood vessel to perform certain procedures to eliminate or reduce the occurrence of embolization. For example, during cardiac bypass surgery, the aorta is both clamped and cannulated. According to methods disclosed herein, the step of clamping may be replaced by deployment of a balloon occluder. These procedures frequently dislodge atheromatous material already present on the walls of the aorta. To minimize the amount of atheromatous material dislodged, a user may clamp or cannulate a section of the aorta which contains the least amount of atheromatous material, as identified by TEE, epicardial aortic ultrasonography or other visualization technique such as intravascular ultrasonography.

Procedures other than incising and clamping also tend to dislodge atheromatous material from the walls of vessels. These procedures include, but are not limited to, dilatation, angioplasty, and atherectomy.

Visualization techniques also may be used to select appropriate sites for filtering blood. Once atheromatous material is located within a vessel, a blood filter device may be placed downstream of that location.

Visualization techniques, other than those already mentioned, as are known to those skilled in the art, are also useful in ascertaining the contours of a blood vessel affected by surgical procedure to assess a variety of risk of embolization factors, and to locate appropriate sections of a vessel for performing certain procedures. Any suitable visualization device may be used to evaluate the efficacy of a device, such as those disclosed herein, in trapping emboli.

In one embodiment, a balloon aortic cannula with associated filter is provided as depicted in FIG. 1. The balloon aortic cannula may include a pressurizing cannula 50 having a proximal region, a distal region, and an intermediate region which connects the proximal and distal regions. The pressurizing cannula 50 is typically a rigid or semi-rigid, preferably transparent tube having a first substantially cylindrical lumen which extends from the proximal region to the distal region and is shaped to receive blood supply cannula 10 or an additional side port (not shown). The pressurizing cannula 50 may further include a second lumen 60 in fluid communication with balloon occluder 65 disposed about the distal region of pressurizing cannula 50. With reference to FIG. 1, balloon occluder 65 is shown in the deflated, contracted condition, having a minimal cross-sectional diameter for entry through an incision in aorta 99. Lumen 60 is adapted to inflate balloon occluder 65 by use of a gas, or preferably saline, under pressure. The proximal end of the cannula 50 may include any of the features disclosed in U.S. application Ser. Nos. 08/553,137, 08/580,223, and 08/584,759.

Blood supply cannula 10, may have certain features in common with a standard arterial cannula and is generally a substantially cylindrical, semi-rigid, and preferably transparent tube. The blood cannula is slidable within the pressurizing cannula, and the blood cannula will typically include a fitting or molded joint at its proximal end (not shown) which is adapted for coupling to a bypass-oxygenator system, and may have any of the features disclosed in U.S. application Ser. Nos. 08/553,137, 08/580, 223, and 08/584,759. Blood cannula 10 is adapted to carry blood to the aorta from the bypass-oxygenator system.

With reference to FIG. 1, the distal region of pressurizing cannula 50 is shown with blood filtration means deployed in the ascending region of a human aorta 99. The distal region of pressurizing cannula 50 includes a plurality of spokes or holding strings 55 made from Dacron® or other suitable material. Holding strings 55 connect the distal region of the pressurizing cannula 50 to an expansion means 70, preferably an inflation seal which comprises a continuous ring of thin tubing attached to filter mesh 75 on its outer side. Filter mesh 75 is bonded at its distal end around the circumference of blood cannula 10, preferably at a cross-sectional position near the distal end of blood cannula 10.

Inflation seal 70 may be constructed from elastomeric or non-elastomeric tubular material which encloses a donut-shaped chamber. When deployed, the inflation seal will expand to a diameter which fits tightly against the lumen of aorta 99. The inflation seal will thus be capable of expansion to an outer diameter of at least 1 cm, more preferably at least 1.5 cm, more preferably at least 2 cm, more preferably at least 2.5 cm, more preferably at least 3 cm, more preferably at least 3.5 cm, more preferably at least 4 cm, more preferably at least 4.5 cm, more preferably at least 5 cm, more preferably at least 5.5 cm, more preferably at least 6 cm. These ranges cover suitable diameters for both pediatric use and adult use. The inflation seal is typically a continuous ring of very thin tubing attached on one side to the filter mesh and on the other side to the pressurizing cannula by holding strings.

The inflation seal should be able to maintain an internal pressure in chamber 319, without bursting, of greater than 55 mm Hg, more preferably greater than 60 mm Hg, more preferably greater than 70 mm Hg, more preferably greater than 80 mm Hg, more preferably greater than 90 mm Hg, more preferably greater than 100 mm Hg, more preferably greater than 110 mm Hg, more preferably greater than 120 mm Hg, more preferably greater than 130 mm Hg, more preferably greater than 140 mm Hg, more preferably greater than 150 mm Hg. The internal pressure needed will depend on the pressure maintained in the aorta against the mesh. Thus, if the aortic pressure is 55 mm Hg, then the pressure in the inflation seal must be greater than 55 mm Hg to prevent leakage around the seal. Typically, the aortic pressure will be at least 75 mm Hg because this level of pressure is needed to ensure adequate brain perfusion. It will be recognized that such inflation seal pressures are much higher than the maximum level that can be used in the pulmonary venous system because the veins and arteries therein will typically hold no more than about 40–50 mm Hg, or at most 60 mm Hg without rupture.

Chamber 71 is in fluid communication with a first tubular passage 56 and a second tubular passage 57 which permit chamber 71 to be inflated with gas, or preferably a fluid such as saline. Passage 57 is in fluid communication with a third lumen of pressurizing cannula 50 (not shown), while passage 56 is in fluid communication with a fourth lumen of pressurizing cannula 50 (not shown). Passages 56 and 57 thereby interconnect chamber 71 with the third and fourth lumens, respectively, of pressurizing cannula 50.

In certain embodiments, inflation seal 70 will include a septum (not shown) which blocks the movement of fluid in one direction around chamber 71. If the septum is positioned in close proximity to the fluid entry port, then the injection of fluid will push all gas in chamber 71 around inflation seal 70 and out through passage 56. In one embodiment, the entry port and the exit port are positioned in close proximity, with the septum disposed between the entry and exit port. In this case, injection of fluid will force virtually all gas out of inflation seal 70.

Filter mesh 75 is bonded at its proximal end to inflation seal 70 and at its distal end to blood cannula 10. Mesh 75 can be made of a material which is reinforced or non-reinforced. Mesh 75, when expanded as shown in FIG. 1, may assume a substantially conical shape with a truncated distal region. The mesh should be formed of a material having a pore size which obstructs objects 5 mm in diameter or less, more preferably 3 mm in diameter, more preferably less than 3 mm, more preferably less than 2.75 mm, more preferably less than 2.5 mm, more preferably less than 2.25 mm, more preferably less than 2 mm, more preferably less than 1.5 mm, more preferably less than 1 mm, more preferably less than 0.75 mm, more preferably less than 0.5 mm, more preferably less than 0.25 mm, more preferably less than 0.1 mm, more preferably less than 0.075 mm, more preferably less than 0.05 mm, more preferably less than 0.025 mm, more preferably 0.02 mm, and down to sizes just larger than a red blood cell. It will be understood that for a given pore size that blocks particles of a certain size as stated above, that pore size will block all particles larger than that size as well. It should also be understood that the necessary pore size is a function of blood throughput, surface area of the mesh, and the pressure on the proximal and distal side of the mesh. For example, if a throughput of 5–6 L/min. is desired at a cross-section of the aorta having a diameter of 40 mm, and a pressure of 120 mm Hg will be applied to the proximal side of the mesh to obtain a distal pressure of 80 mm Hg, then a pore size of about $\geq 50$ $\mu$m is needed. By contrast, in the pulmonary artery the same throughput is needed, but the artery cross-section has a diameter of only 30 mm. Moreover, the proximal pressure is typically 40–60 mm Hg, while the distal pressure is about 20 mm Hg. Thus, a much larger pore size is needed to maintain blood flow. If pore sizes as disclosed herein for the aorta were used in the pulmonary artery, the blood throughput would be insufficient to maintain blood oxygenation, and the patient would suffer right ventricular failure because of pulmonary artery hypertension.

Figure 2A:
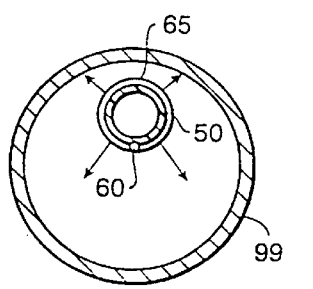
FIGS. 2A, 2B, and 2C are cross-sectional views through section line 2—2 of the device depicted in FIG. 1, showing the balloon occluder at successive degrees of inflation.
Figure 2B:
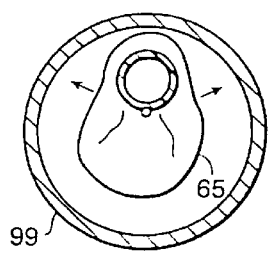
Figure 2C:
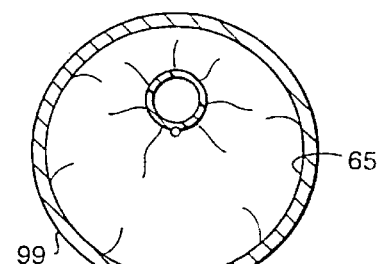
Figure 3:
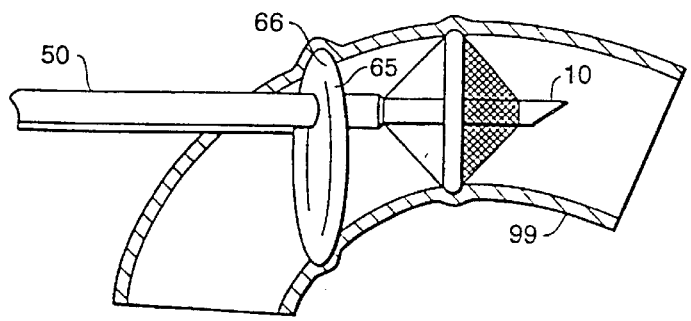
FIG. 3 is a longitudinal view of the balloon aortic cannula depicted in FIG. 1, showing the balloon occluder in the fully expanded condition and disposed circumferentially about the blood cannula.

Much like the inflation seal, the balloon occluder 65 may be constructed from elastomeric or non-elastomeric material and, with reference to FIG. 3, comprises a continuous ring of tubing which encloses a tubular chamber 66 disposed circumferentially about the pressurizing cannula 50 and blood cannula 10. FIGS. 2A, 2B, and 2C illustrate deployment of balloon occluder 65 within aorta 99. When pressurized saline passes through lumen 60, balloon occluder 65 expands to a diameter which fits tightly against the inner wall of aorta 99. The balloon occluder will thus be capable of expansion to an outer diameter of at least 1 cm, more preferably at least 1.5 cm, more preferably at least 2 cm, more preferably at least 2.5 cm, more preferably at least 3 cm, more preferably at least 3.5 cm, more preferably at least 4 cm, more preferably at least 4.5 cm, more preferably at least 5 cm, more preferably at least 5.5 cm, more preferably at least 6 cm. FIG. 3 depicts a longitudinal view of the balloon aortic cannula with balloon occluder 65 fully expanded within aorta 99 and thereby occluding retrograde flow of blood in the ascending aorta.

With reference to FIG. 3, balloon occluder 65 should be able to maintain an internal pressure in chamber 66, without bursting, of greater than 55 mm Hg, more preferably greater than 60 mm Hg, more preferably greater than 70 mm Hg, more preferably greater than 80 mm Hg, more preferably greater than 90 mm Hg, more preferably greater than 100 mm Hg, more preferably greater than 110 mm Hg, more preferably greater than 120 mm Hg, more preferably greater than 130 mm Hg, more preferably greater than 140 mm Hg, more preferably greater than 150 mm Hg. The internal pressure needed will depend on the pressure maintained in the aorta against the balloon occluder. Thus, if the aortic pressure is 55 mm Hg, then the pressure in the balloon occluder must be greater than 55 mm Hg to prevent leakage around the balloon occluder. Typically, the aortic pressure will be at least 75 mm Hg because this level of pressure is needed to ensure adequate brain perfusion. It will be recognized that such balloon occluder pressures are much higher than the maximum level that can be used in the pulmonary venous system because the veins and arteries therein will typically hold no more than about 40–50 mm Hg, or at most 60 mm Hg without rupture.

In certain embodiments, the pressurizing cannula 50 will be provided with an additional lumen (not shown) in fluid communication with balloon occluder 65. A system having two lumens in communication with balloon occluder 65 can be used to enter saline into the balloon occluder and purge all gas therefrom to prevent the formation of an air embolism in a patient's circulation should the balloon occluder rupture during use. Thus, if pressurized saline is advanced through lumen 60, the gas present in balloon occluder 65 will be forced out through the additional lumen in communication with the balloon occluder. A septum may be included in the balloon occluder and disposed between entry and exit ports to ensure that all gas is purged on entry of saline.

It will also be understood for this cannula apparatus that blood flow to the patient is maintained by blood passage through blood cannula 10, and not through mesh 75. Thus, the cannula must have an inner diameter which allows blood throughput at a mean flow rate of at least 3.0 L/min., more preferably 3.5 L/min., more preferably 4 L/min., more preferably at least 4.5 L/min., more preferably at least 5 L/min., and more. Of course, flow rate can vary intermittently down to as low as 0.5 L/min. Therefore, the inner diameter of blood supply cannula 10 will typically be at least 9 F (3.0 mm), more preferably 10 F, more preferably 11 F, more preferably 12 F (4 mm), more preferably 13 F, more preferably 14 F, more preferably 15 F (5 mm), and greater. Depending on the inner diameter and thickness of the tubing, the outer diameter of blood cannula 10 is approximately 8 mm. Meanwhile, the pressurizing cannula 50 may have an outer diameter of approximately 10.5 mm. The foregoing ranges are intended only to illustrate typical device parameters and dimensions, and the actual parameters may obviously vary outside the stated ranges and numbers without departing from the basic principles disclosed herein.

In use, the balloon aortic cannula with associated filter is provided, and saline is injected into both the balloon occluder and the inflation seal until saline exits from the exit ports and exit lumens, thereby purging substantially all gas from the inflation seal, the balloon occluder, and dual lumen systems associated with each. Cardiac surgery can then be conducted in accordance with procedures which employ standard cannula insertion, as discussed more fully herein. The mesh 75, inflation seal 70, and balloon occluder 65 are maintained in a deflated, fully contracted condition about the pressurizing cannula and/or blood cannula. The cannula is introduced into the aorta, preferably the ascending aorta, of a patient through an incision, and the incision may be tightened about the cannula by use of a "purse string" suture. Cardiopulmonary bypass occurs through blood cannula 10.

With the cannula in place, the filter is ready for deployment. The filtration means are first exposed by removing a handle or enclosure which may cover the expansion means and mesh. Then, saline or gas is advanced under pressure through lumen 57 to expand the inflation seal. The inflation seal expands to ensure contact with the inside of the aorta at all points along the circumference of the lumen, as depicted in FIGS. 1 and 2C. The inflation system for the expansion means is then locked in place to prevent inflation or depressurization of the inflation seal during use.

The balloon occluder 65 is then deployed to occlude the aorta upstream of the filter. Saline or gas is advanced under pressure through lumen 60 to expand the balloon occluder, as shown in FIGS. 2A, 2B, 2C, and 3. Embolic material dislodged from the aorta is captured by filter mesh 75. The bypass-oxygenator system is then started to achieve cardiopulmonary bypass through blood cannula 10. Cardiac surgery is performed while the filter, inflation seal, and balloon occluder are maintained in place for a number of hours, typically 8 hours or less, more typically 7 hours or less, more typically 6 hours or less, more typically 5 hours or less, more typically 4 hours or less, more typically 3 hours or less, more typically 2 hours or less, and more typically 1 hour or less.

At the end of the cardiac surgery, the balloon occluder is depressurized, and any embolic material dislodged by this step is captured by the filter. The filter is then depressurized and removed from the ascending aorta. The syringe lock is released and saline is withdrawn from the balloon occluder, and then from the inflation seal. This will cause both the balloon occluder and inflation seal to contract to a deflated condition with minimum cross-sectional diameter, as the device was configured before deployment. Notably, embolic material collected in the filter is trapped under the contracted filter. Once the inflation seal, associated filter, and balloon occluder have been deflated, the cannula can be removed from the patient without damaging the aortic incision by using standard procedures.

The devices disclosed herein may optionally include a handle adapted to cover and enclose the inflation seal, mesh, and balloon occluder. Moreover, before deployment, the inflation system for either the balloon occluder, inflation seal, or both, may be carried by either the pressurizing cannula or the blood cannula. In certain embodiments, the blood cannula and pressurizing cannula will be integrally combined into a single unitary component, or the pressurizing cannula is eliminated and the inflation system may be carried either within or on the outside of the blood cannula.

Figure 4:
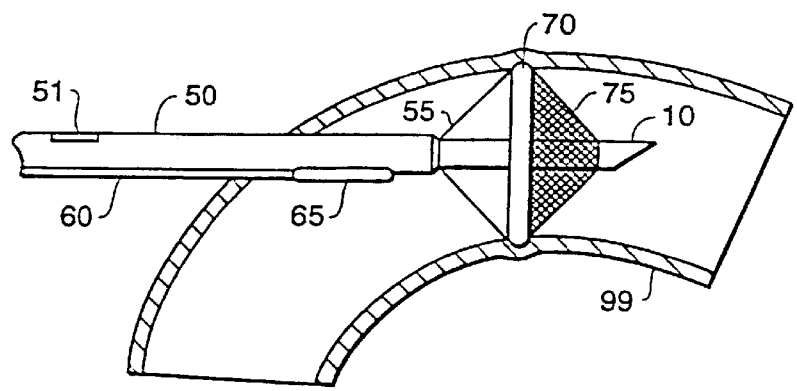
FIG. 4 is a longitudinal view of a balloon aortic cannula according to another embodiment, showing the filter deployed and the balloon occluder in the contracted condition at a radial position about the distal region of the balloon aortic cannula.

In another embodiment, a balloon aortic cannula is provided as depicted in FIG. 4, with balloon occluder 65 disposed at one radial position on a side of pressurizing cannula 50. It will be understood that FIG. 4 shares many features in common with FIGS. 1 and 3, and the numbering of apparatus components has been duplicated so that appropriate description can be found with reference to FIGS. 1 and 3. With reference to FIG. 4, balloon occluder 65 is shown in the deflated, contracted state on a side of pressurizing cannula 50 and disposed about the distal region thereof. Rotational orientation marker 51 may be included in certain embodiments and disposed at a fixed radial position relative to the point of attachment of balloon occluder 65, e.g., at a radial position 180° from balloon occluder 65. The inclusion of a marker on the proximal region of the pressurizing cannula 50 will enable rotation of the cannula once inserted in the aorta in order to ensure positioning of balloon occluder 65 so that expansion and balloon occlusion occurs upstream of filter 75, and does not interfere with blood cannula 10 and/or pressurizing cannula 50. Alternatively, where the pressurizing cannula 50 or blood cannula 10 includes a lumen 60 which is visible on the exterior sheath, the lumen 60 may be used as a rotational orientation marker.

Figure 5:
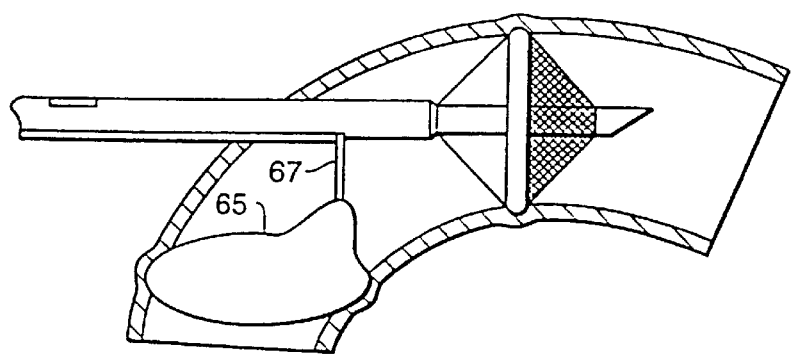
FIG. 5 is a longitudinal view of the balloon aortic cannula according to FIG. 4, showing the balloon occluder and filter deployed after insertion of the cannula into the aorta.
Figure 6:
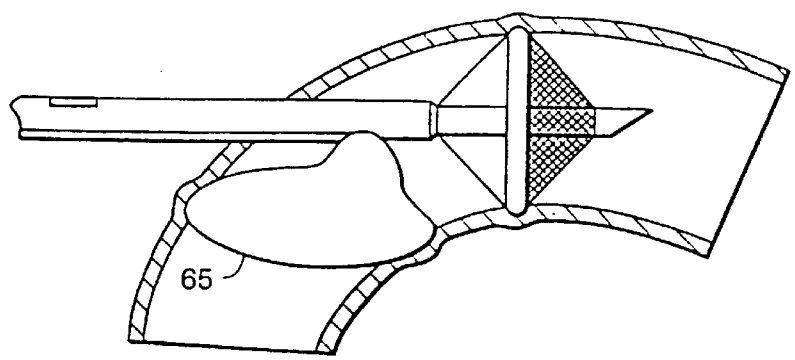
FIG. 6 is a longitudinal view of a balloon aortic cannula according to another embodiment.

Upon inflation, balloon occluder 65 assumes a shape as depicted in FIGS. 5 or 6. With reference to FIG. 5, the occlusion chamber 65 is shown connected to the cannula by way of a tubular extension 67 which distances the balloon occluder from the cannula. Alternatively, as shown in FIG. 6, the chamber of balloon occluder 65 may be in close contact with pressurizing cannula 50 or blood cannula 10.

It will be understood that the balloon occluders as disclosed herein and depicted on balloon aortic cannulas may be used in combination with any of a number of arterial cannulas having associated filtration means as previously disclosed. Thus, the balloon occluders disclosed herein can be used in combination with any of the arterial cannulas disclosed in Barbut et al., U.S. application Ser. No. 08/584,759, filed Jan. 9, 1996, Barbut et al., U.S. application Ser. No. 08/580,223, filed Dec. 28, 1995, Barbut et al., U.S. application Ser. No. 08/553,137, filed Nov. 7, 1995, Barbut et al., U.S. Pat. No. 5,769,816, filed Apr. 30, 1996, Barbut et al., U.S. Pat. No. 5,989,281, filed Apr. 16, 1997, and Maahs et al., U.S. Pat. No. 5,846,260, filed May 8, 1997, and any of the features disclosed in these applications can be used on the balloon aortic cannulas described herein. Accordingly, the entire disclosures of these prior applications are incorporated herein by reference, and it is noted that the devices, methods, and procedures disclosed in these applications can be used in combination with the balloon occluder and balloon aortic cannula disclosed herein.

Figure 7:
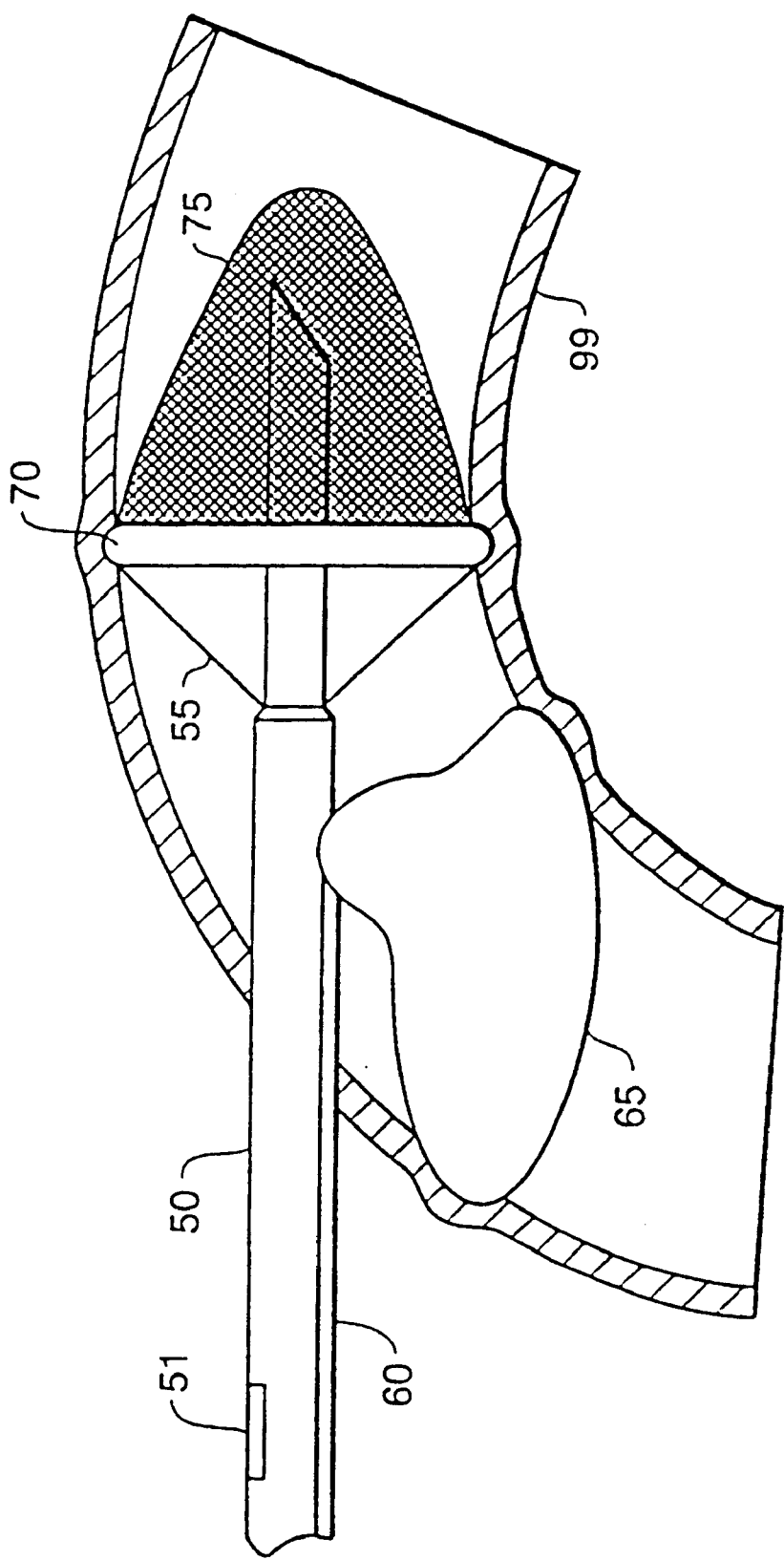
FIG. 7 is a longitudinal view of a balloon aortic cannula according to another embodiment, wherein the filter mesh is continuous.
Figure 8:
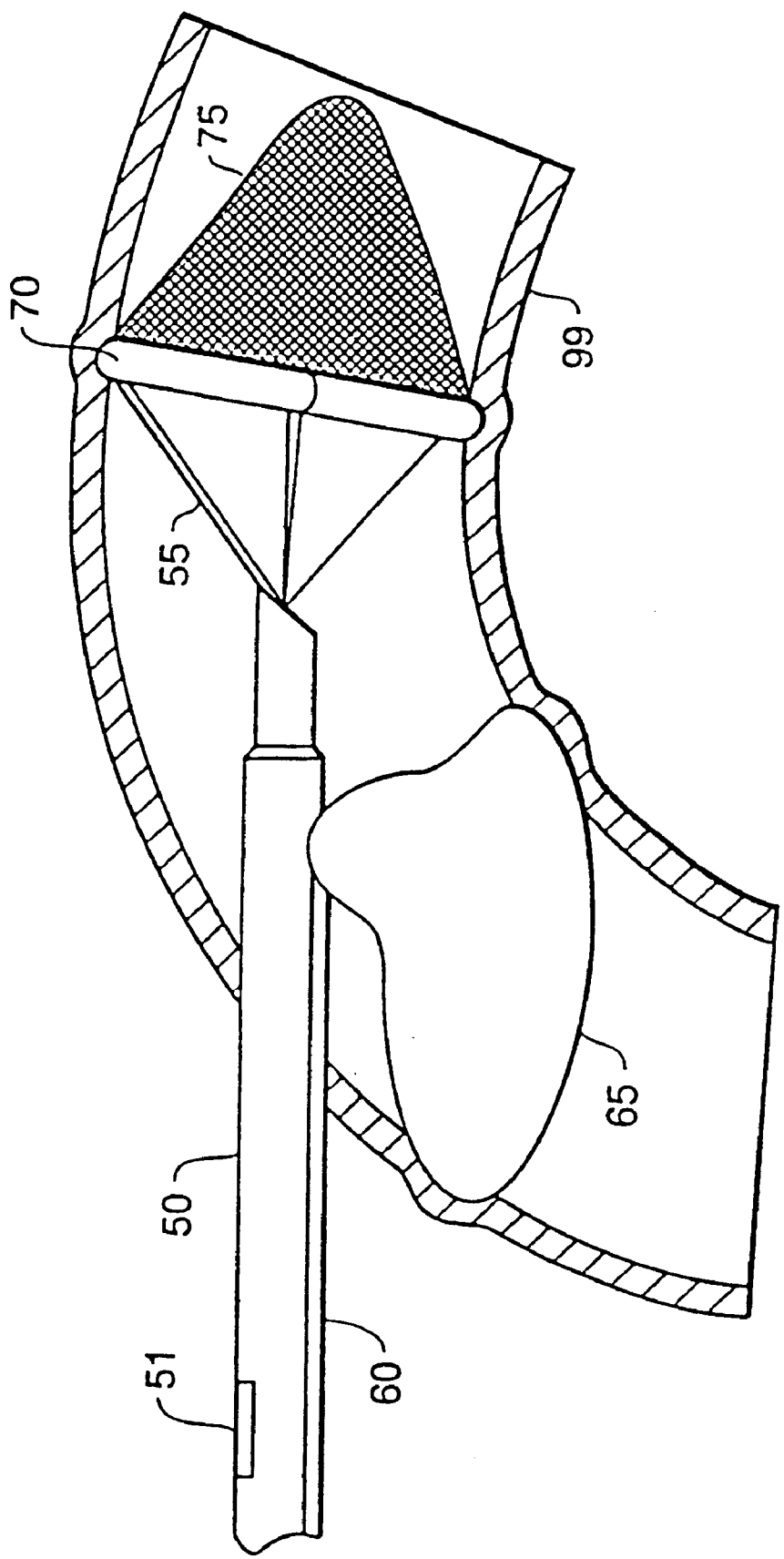
FIG. 8 is a longitudinal view of a balloon aortic cannula according to another embodiment.

In another embodiment, a cannula is provided as depicted in FIG. 7 with a continuous filter mesh which extends beyond and over the lumen of the blood cannula so that blood from the cannula passes through the mesh before circulating within the patient. The device may include a pressurizing cannula 50, a blood cannula, inflation seal 70, continuous mesh 75, and balloon occluder 65 which operates upstream of mesh 75. In still another embodiment, the continuous filter mesh is tethered from the distal end of cannula 50 by a plurality of holding strings 55, as depicted in FIG. 8. It will be understood that FIGS. 7 and 8 share many features in common with FIGS. 4 and 6, and the numbering of apparatus components has been duplicated so that appropriate description can be found with reference to FIGS. 4 and 6.

In anther embodiment, a balloon aortic cannula is provided as depicted in FIG. 9. The device includes a pressurizing cannula 300 having proximal region 301, distal region 302, and an intermediate region which connects the proximal and distal regions. The pressurizing cannula 300 is typically a rigid or semi-rigid, preferably transparent tube having a first substantially cylindrical lumen 303 which extends from the proximal region and is shaped to receive blood supply cannula 350. The pressurizing cannula 300 further includes at its proximal region luer fittings 304 and 305 which are shaped to receive a cap or septum 306 and a syringe 307 filled with saline or gas and having a locking mechanism 308 for locking the barrel 309 and plunger 310 in a fixed position. The pressurizing cannula 300 typically has a dual lumen to affect pressurization of the inflation seal. Thus, luer 305 is connected to passage 311 which is in fluid communication with a second lumen 312 which extends from the proximal to the distal end of pressurizing cannula 300. Meanwhile, luer 304 is connected to passage 313 which is in fluid communication with a third lumen 314 which extends from the proximal to the distal end of pressurizing cannula 300. At its distal region, the pressurizing cannula 300 includes a blood filtration assembly 315.

Blood supply cannula 350 may have certain features in common with a standard cannula, and is generally a substantially cylindrical, semi-rigid, and preferably transparent tube which includes a rib 351 disposed about the circumference at a distal region thereof. The blood cannula is slidable within the pressurizing cannula, and in the proximal region, the blood cannula 350 may be angled to adopt a shape which does not interfere with syringe 307. Moreover, the blood cannula will typically include a fitting or molded joint 352 which is adapted for coupling to a bypass-oxygenator system. Blood cannula 350 is adapted to carry blood to the aorta from the bypass-oxygenator system.

The pressurizing cannula may also include an inserting and retracting handle 380 comprising a substantially cylindrical tube disposed about the intermediate region of pressurizing cannula 300. Handle 380 will generally include a rigid or semi-rigid, preferably transparent tube with molded hand grip to facilitate holding and inserting. With reference to FIG. 9, handle 380 is slidable relative to the pressurizing cannula 300, and may include a sealing member 381 comprising a rubber washer or O-ring mounted in a proximal region of the handle and disposed between 380 and pressurizing cannula 300 to prevent leakage of blood therebetween. Handle 380 may include corrugation ribs 382 in its proximal and intermediate regions, and a substantially flat or level collar insertion region 383 adapted to fit tightly against vessel material at an aortic incision. In certain embodiments, collar insertion region 383 will include a sealing ring or rib (not shown), having a width of about 5 mm and an outer diameter of about 13 mm, which serves as an anchor against the aorta to prevent the cannula assembly from slipping out during a surgical procedure. A "purse string" suture is generally tied around the circumference of the aortic incision, and this string will be tightened around the ring in collar region 383 to prevent slippage of the cannula assembly.

Handle 380 may also include an enlarged end region 384 which encloses the blood filtration assembly 315 as described in Barbut et al., U.S. Pat. No. 5,769,816, filed Apr. 30, 1996. This housing enclosure 384 is a particularly preferred component because it prevents inadvertent deployment of the blood filtration assembly and balloon occluder, and it provides a smooth outer surface to the cannula which facilitates entry through an incision in the aorta without tearing the aorta. In the absence of such housing enclosure, the balloon and filter are liable to scrape against the inner wall of a vessel, and thereby damage or rupture the vessel. At its distal end, handle 380 may include inverted cuff 385 which bears against rib 351 of blood cannula 350 to form a seal when the filtration assembly 315 is enclosed by handle 380.

The distal region of pressurizing cannula 300 is shown with blood filtration assembly 315 deployed in the ascending aorta 399 of a human. Handle 380 has been moved proximally to expose filter assembly 315. The distal region of pressurizing cannula 300 includes a plurality of holding strings 316 made from Dacrong or other suitable material. Holding strings 316 connect the distal region of the pressurizing cannula 300 to inflation seal 317 as described above. The inflation seal is attached to filter mesh 318 on its outer side. Filter mesh 318 is bonded at its distal end around the circumference of blood cannula 350 preferably at a cross-sectional position which closely abuts rib 351.

Chamber 319 is in fluid communication with a first tubular passage 320 and a second tubular passage 322 which permit chamber 319 to be inflated with gas, or preferably a fluid such as saline. Passage 320 is in fluid communication with second lumen 312 of pressurizing cannula 300, while passage 322 is in fluid communication with third lumen 314 of pressurizing cannula 300. Passages 320 and 322 thereby interconnect chamber 319 with the second and third lumen 312 and 314, respectively, of pressurizing cannula 300.

In certain embodiments, inflation seal 317 will include a septum 321 which blocks the movement of fluid in one direction around chamber 319. If septum 321 is positioned in close proximity to the fluid entry port, then the injection of fluid will push all gas in chamber 319 around inflation seal 317 and out through passage 322, as described above. In one embodiment, the entry port and the exit port are positioned in close proximity with septum 321 disposed between the entry and exit port. In this case, injection of fluid will force virtually all gas out of inflation seal 317.

With reference to FIG. 9, the pressurizing cannula 300 may further include balloon occluder 65 operably attached at a distal region of pressurizing cannula 300, and generally proximal to the filtration assembly 315. Balloon occluder 65 will, upon inflation, expand upstream of the aortic incision and filtration assembly 315 to occlude a region of the ascending aorta as described above. In those embodiments which include handle 380, balloon occluder 65 will pass through an opening in handle 380 in order to define a chamber which is in fluid communication with an additional, fourth lumen (not shown) of pressurizing cannula 300. A cross-sectional view of pressurizing cannula 300 and handle 380 in the region of balloon occlude 65 is depicted in FIG. 9A. With reference to FIG. 9A, balloon occluder 65 passes through opening 386 in handle 380.

Figure 10:
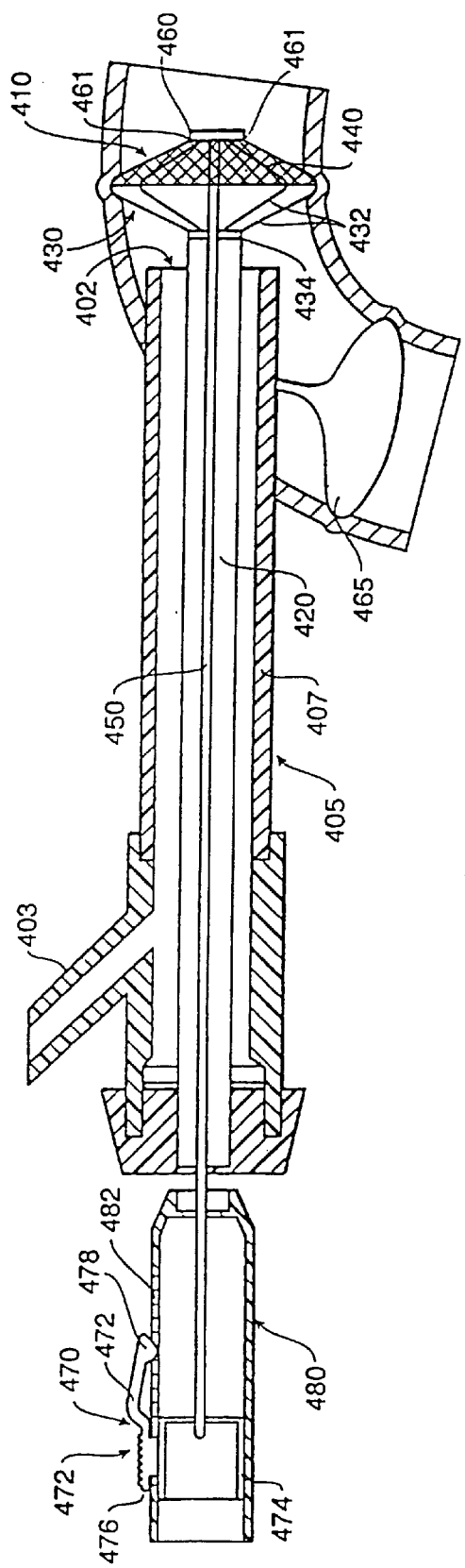
FIG. 10 is a longitudinal view of a balloon aortic cannula according to another embodiment.

In yet another embodiment, a balloon aortic cannula is provided as depicted in FIG. 10. The device includes blood filtration system 410 which comprises insertion tube 420, umbrella frame 430, end plate 460, activation tube 450, mesh 440, adjustment device 470, and handle 480. Filtration assembly 410 is introduced into a vessel through main port 407 of cannula 405, and blood or other surgical equipment may be introduced into main port 407 of cannula 405 through side port 403. The cannula 405 and filtration system 410 will not interfere with placement of equipment which may be used during a surgical procedure.

Umbrella frame 430 comprises a plurality of arms 432 (some of which are not shown), which may include 3 arms, more preferably 4 arms, more preferably 5 arms, more preferably 6 arms, more preferably 7 arms, more preferably 8 arms, more preferably 9 arms, and most preferably 10 arms. Socket 434 may be connected to insertion tube 420 by welding, epoxy, sonic welding, or adhesive bonding. A further detailed description of the construction of filtration assembly 410 can be found with reference to Barbut et al., U.S. application Ser. No. 08/584,759, filed Jan. 9, 1996, and other references cited herein.

End plate 460 comprises a one-piece injection molded component, made of plastic or metal. Arms 432 are bonded to end plate 460 at arm junctures 461 spaced at equal increments along a circumference of a circle. Activation tube 450 extends from end plate 460 through insertion tube 420 to adjustment device 470 housed in handle 480 as shown in FIG. 10. Adjustment device 470 is a linear actuation device, comprising thumb switch 472 which is attached to guide frame 474 which is in turn attached to activation tube 450 via a bond joint. Thumb switch 472 comprises base 476 and rachet arm 478 which moves along rachet slot 482 along the top of handle 480, locking in predetermined intervals in a manner known in the art. Sliding thumb switch 472 away from distal end 402 of cannula 405 retracts activation tube 450, which in turn draws end plate 460 toward handle 480. This movement causes arms 432 of umbrella frame 430 to bend and causes mesh 440 to open and ready to capture embolic material in the blood. Sliding thumb switch 472 toward distal end 402 of cannula 405 pushes activation tube 450 in the direction of mesh 440. Activation tube 450 then pushes end plate 460 away from handle 480, causing arms 432 of umbrella frame 430 to straighten and mesh 440 to close.

With reference to FIG. 10, filtration device 410 further includes balloon occluder 465 connected to a further lumen (not shown) on cannula 405. Accordingly, the assembly provides balloon occluder 465 at a distal region of cannula 405 so that, upon deployment, balloon occluder 465 expands upstream of the filtration assembly, which assembly captures embolic material dislodged upon deployment of balloon 465.

Figure 11:
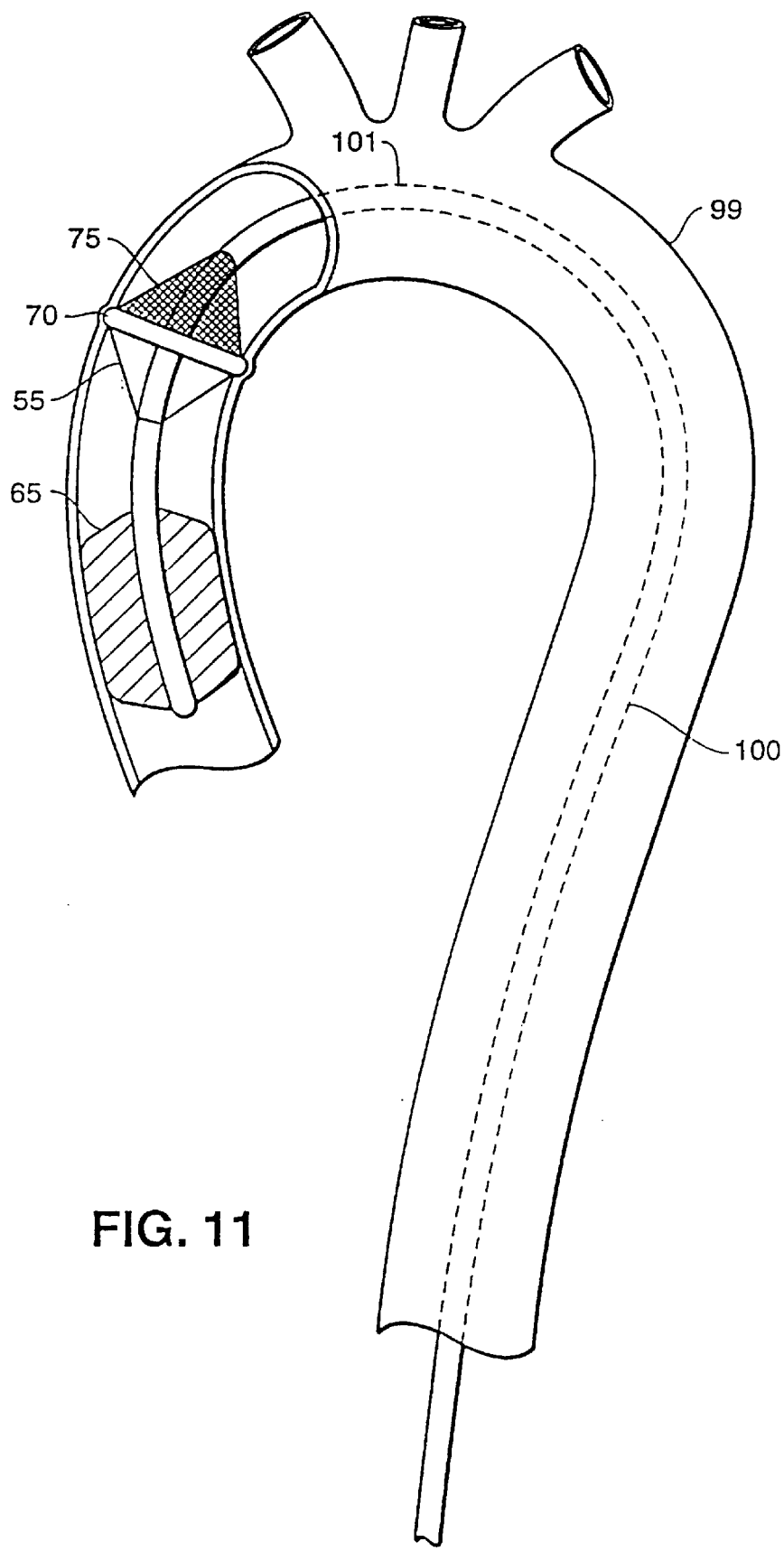
FIG. 11 is a longitudinal view of an arterial balloon catheter disposed within the aorta and having a balloon occluder and filter deployed therein.

In another embodiment, an arterial balloon catheter is provided as depicted in FIG. 11. The catheter includes flexible elongate member 100 having an outer surface, a distal region 101, and a proximal region. The catheter includes balloon occluder 65 at the distal end of the elongate member. The catheter also includes at its distal region expansion means, such as inflation seal 70, filter mesh 75 attached to inflation seal 70, and may optionally include holding strings 55 which secure the inflation seal to catheter 100. The catheter may also include an inflation system (not shown) to operate inflation seal 70, as described above for other embodiments.

Figure 12:
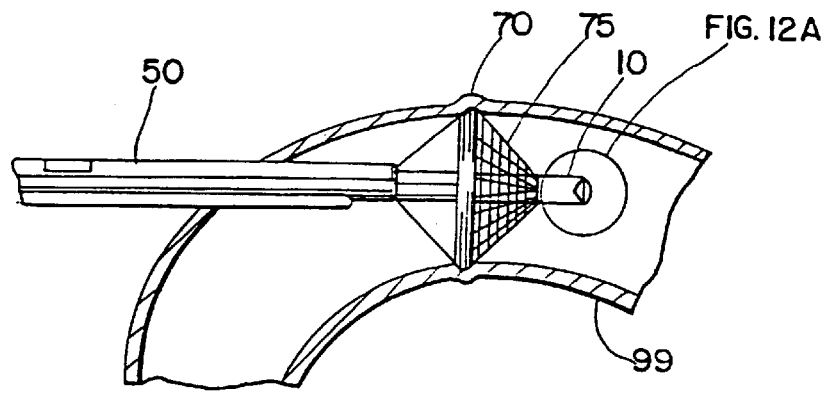
FIG. 12 is a longitudinal view of a balloon aortic cannula according to another embodiment, wherein a flow diffuser is included at a location distal to the filter.
Figure 12A:
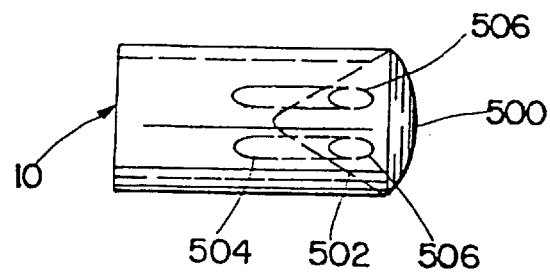
FIG. 12a is a detail of the flow diffuser of FIG. 12.

In another embodiment, an arterial balloon cannula with associated filter and distal flow diffuser is provided as depicted in FIGS. 12 and 12a. In this embodiment the distal end of the cannula 10, is closed with a cap 500 and the flow diffuser is a rounded cone 502 extending inside the lumen of the cannula. As shown in FIG. 12, the cap preferably has a rounded, hemispherical shape to facilitate the insertion of the distal end of the cannula into the vessel. The flow diffuser tapers towards the proximal end of the cannula 10 starting from the end cap. The shape of the flow diffuser is preferably conical in order to avoid damaging the blood. However, other shapes, including pyramidal shapes, may be employed.

As shown in FIG. 12a, a plurality of outlet openings 504 are formed in the sidewall of the cannula 10 adjacent to its distal end. The openings may have an arched configuration, with the curved portion 506 of each arch oriented in the upstream direction. Although any number of openings are possible, a preferred embodiment has six openings. Preferably the total area of the openings is greater than the area of the distal end opening of a conventional catheter of the same diameter. The length of the openings 504 are also preferably greater than the length of the flow diffuser 502.

Figure 13:
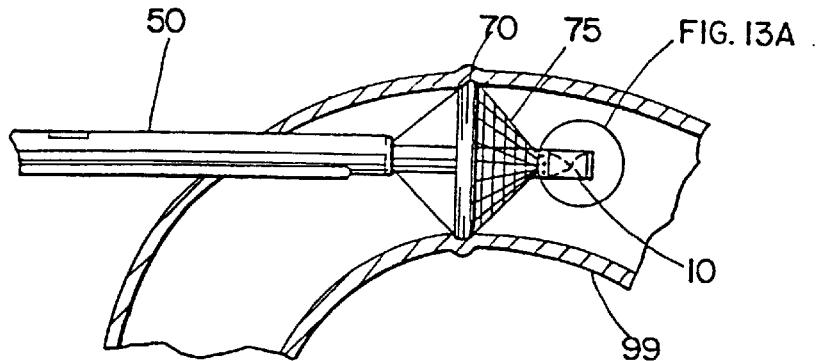
FIG. 13 is a longitudinal view of a balloon aortic cannula according to another embodiment, wherein a flow diffuser is included at a location distal to the filter.
Figure 13A:
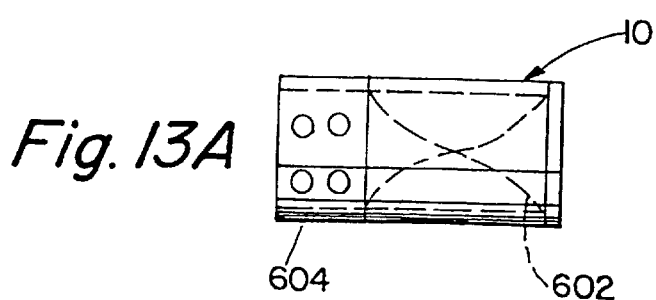
FIG. 13a is a detail of the flow diffuser of FIG. 13.

In another embodiment, an arterial balloon cannula with filtration means is provided as depicted in FIGS. 13 and 13a. In this embodiment, the distal end of the cannula 10 contains a diffuser 602 with a helical configuration. The diffuser 602 can be held in place within the cannula by the tapering configuration of the distal end of the cannula, by adhesives, by ultrasonic welding, or by some other suitable means. The diffuser is preferably formed from a flat rectangular member with a single one-hundred-eighty degree twist. In this embodiment, the distal end of the cannula is partially blocked. Additionally, any number of outlet opening 604 may be formed in the sidewall of the cannula.

The intra-cannula flow diffusers of FIG. 12 and FIG. 13 may also be employed proximal to the filter by positioning the diffuser within the arterial balloon cannula of FIG. 7. Other variations and details of intra-lumen flow diffusers may be found in Cosgrove et. al., Low Velocity Aortic Cannula, U.S. Pat. No. 5,354,288, which is incorporated by reference herein.

Figure 14:
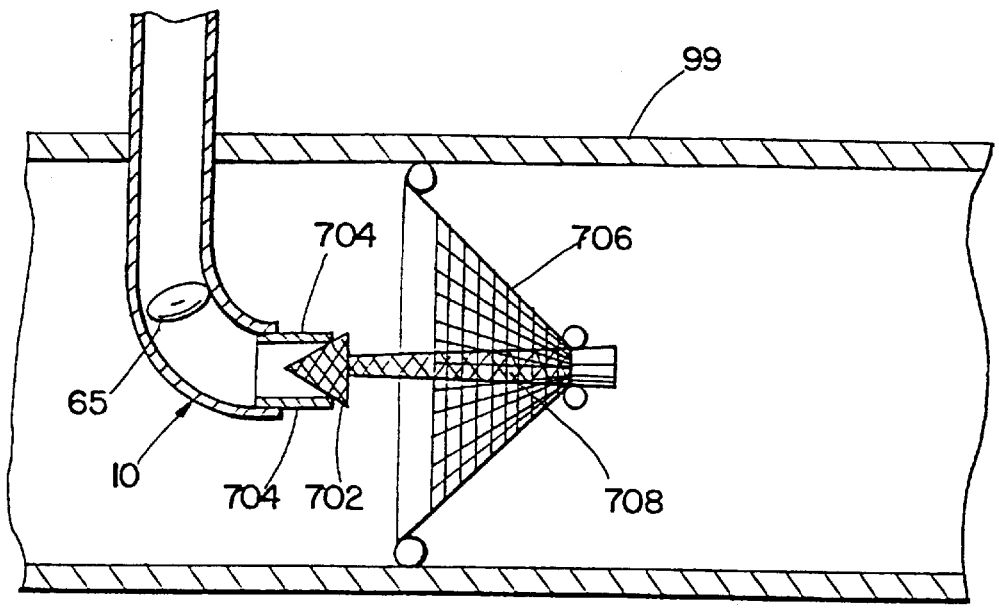
FIG. 14 is a longitudinal view of a balloon aortic cannula according to another embodiment, wherein a flow diffuser is included at a location proximal to the filter.

In another embodiment, an arterial balloon cannula is provided as in FIG. 14. In this embodiment the proximal end of a flow diffuser 702 is connected to the distal end of the cannula 10 by a plurality of structural supports 704. The diffuser 702 is preferably conical, although other shapes may be used. The distal end of the flow diffuser 702 extends to the apex of the filter 706 by virtue of a linear shaft 708 said shaft running through the center of the expanded filter. In this embodiment the flow diffuser 702 diffuses blood flow proximal to the filter 706.

Figure 15:
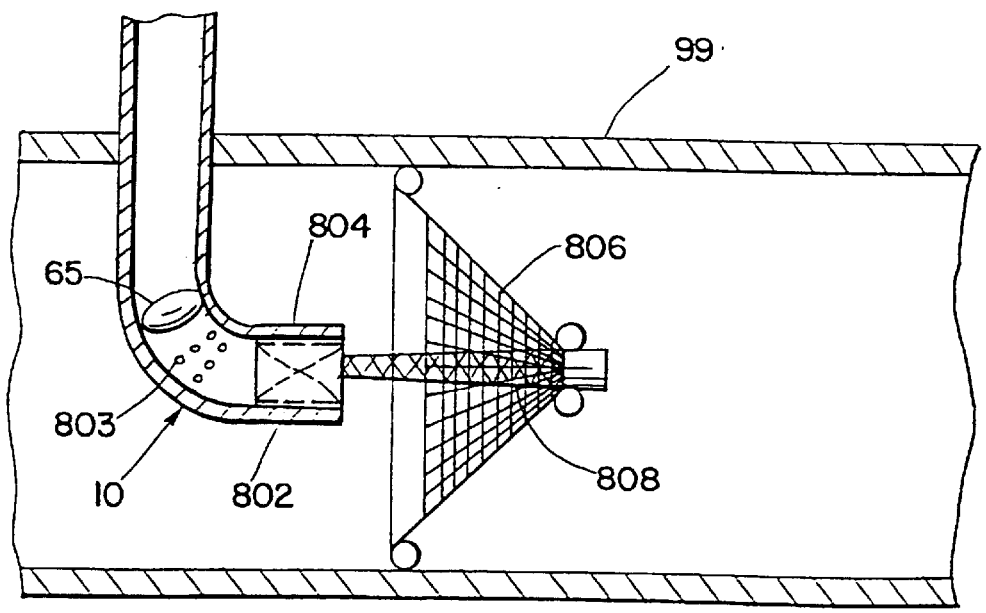
FIG. 15 is a longitudinal view of a balloon aortic cannula according to another embodiment, wherein a flow diffuser is included at a location proximal to the filter.

In another embodiment, an arterial balloon cannula is provided as in FIG. 15. In this embodiment the flow diffuser 802 is contained within the distal end of the blood cannula 10. In a preferred embodiment, the diffuser 802 is the helical diffuser shown in FIGS. 13 and 13a. The flow diffuser 802 can be held in place by the tapering configuration of the distal end of the cannula, by adhesives, by ultrasonic welding, or by some other suitable means. Unlike the invention of FIG. 13, the distal end of the diffuser 802 is attached to the apex of the filter 806 by virtue of a linear shaft 808 said shaft running through the center of the expanded filter. The shaft may be any shape which will not traumatize blood components, and preferably comprises a rounded surface which tapers outward in the distal direction. In this embodiment the flow diffuser diffuses cannula blood flow proximal to the filter. The cannula 10 optionally contains openings 803 in its distal end 804 to further diffuse the cannula blood. In an alternate embodiment, blood diffuser 802 is contained within cannula 10 but is not connected to filter 806 said filter being supported as disclosed in FIG. 7.

Although cannulas have been selected for purposes of example, the inventions of FIGS. 12–15 can be readily applied for use in arterial balloon catheters.

It is to be understood that flow diffusers such as those of FIGS. 12–15 can be used in any blood filter device having a blood supply cannula and associated filter, including the devices depicted in FIG. 3 and FIG. 4. Furthermore, the diffuser of FIG. 15 may be employed inside a cannula having a distal filter, such as in FIG. 7, thus creating a blood filter device with two filters, one proximal to and one distal to the cannula opening.

Figure 16:
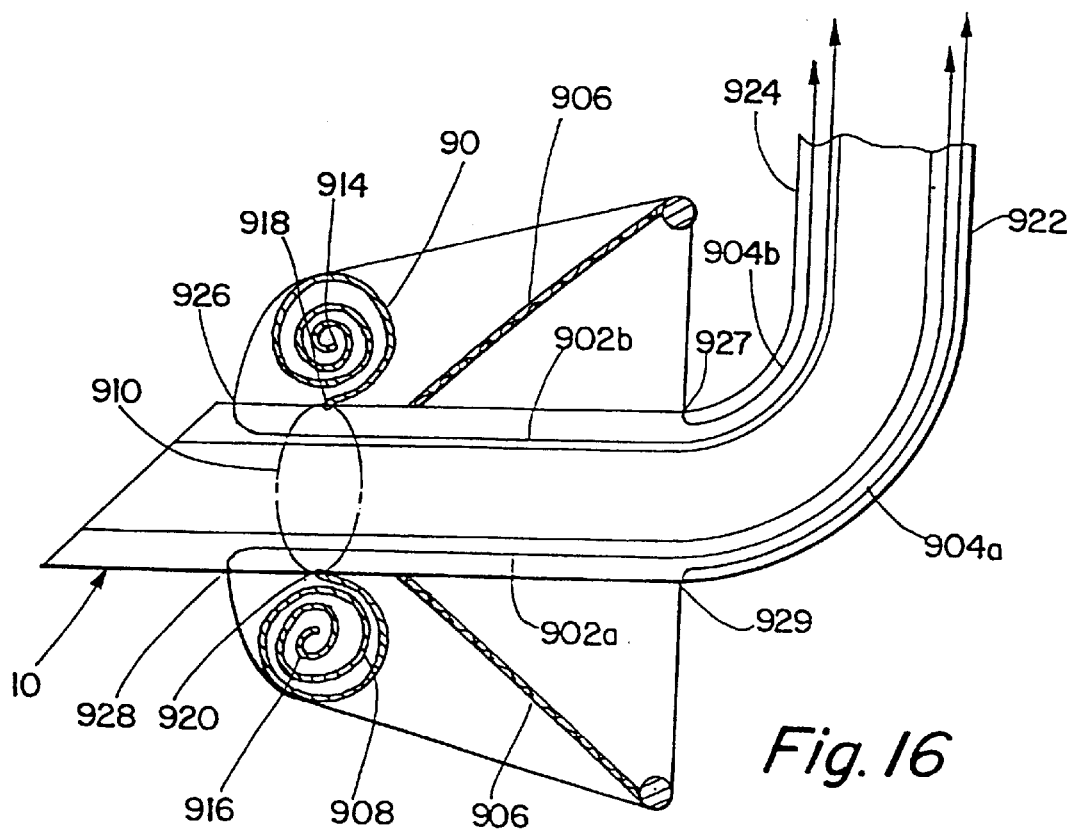
FIG. 16 is a longitudinal view of a balloon aortic cannula according to another embodiment wherein the cannula includes a condom-like filter sleeve shown in a rolled back position.

In an alternative embodiment, shown in FIG. 16, an arterial balloon cannula and associated filter 906 include a generally cylindrical filter sleeve 908 disposed circumferentially about the distal end of the cannula and attached to four control lines 902a, 902b, 904a, 904b. Proximal force on unroll control lines 904a and 904b unrolls filter sleeve 908 from its depicted position so as to capture the filter resulting in the position shown in FIG. 17. In this embodiment, the manner of unrolling the filter sleeve is analogous to the unrolling of a latex condom. Although the sleeve may be any shape, provided it both encases the cannula and rolls up in response to the control lines, in a preferred embodiment the sleeve has a circular cross-section.

In FIG. 16 the filter sleeve 908 is rolled back distal to the filter, to allow the filter to be fully expanded. FIG. 16 shows a cross-sectional cut-away of the sleeve. The full sleeve, not depicted, is a continuous piece surrounding the cannula about a 360 degree radius. In a preferred embodiment, a circular condom-like sleeve is attached at the outer-diameter of the cannula along the arc of circle 910. The condom-like sleeve has a distal opening to permit exit of the cannula tip. In a preferred embodiment a pair of control lines 902a and 904a enter a control lumen at points 928 and 929 respectively and run inside control lumen 922 adjacent the cannula lumen until exiting the control lumen at a proximal point on the cannula (not shown). In the preferred embodiment, a second set of control lines 902b and 904b enter a second control lumen 924 at points 926 and 927 respectively, said points located one-hundred eighty degrees from the first lumen along the cannula's outer diameter.

Figure 17:
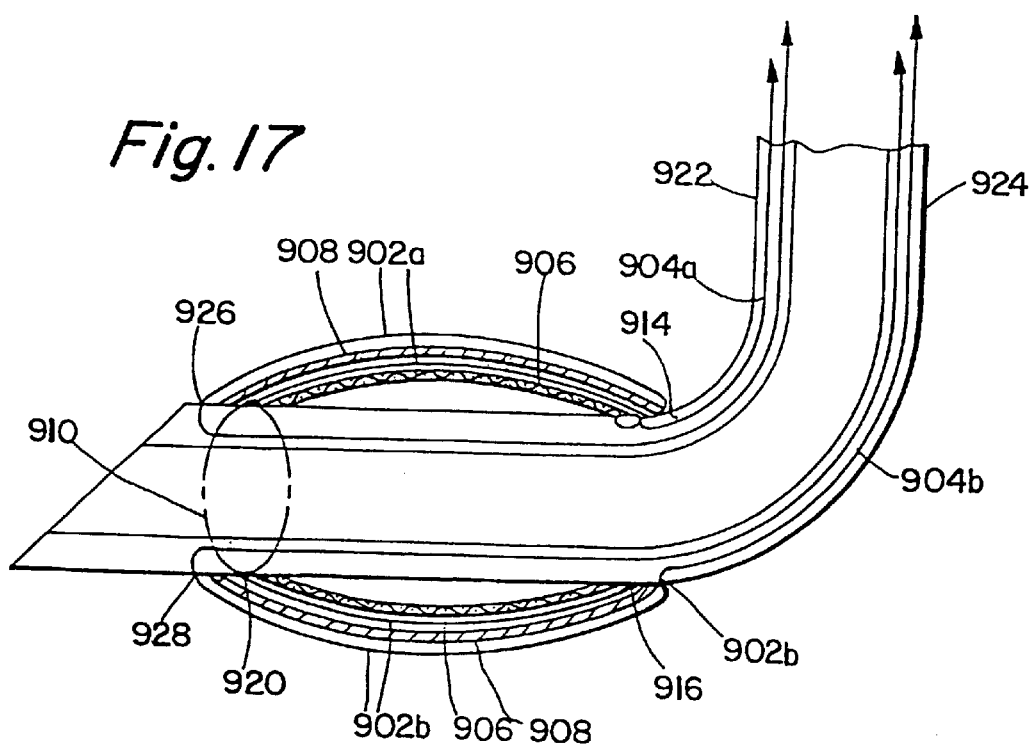
FIG. 17 is a longitudinal view of the balloon aortic cannula of FIG. 16 wherein the unrolled filter sleeve has captured the filter means.

As shown in FIG. 17, unroll control lines 904a and 904b are attached to sleeve 908 at points 914 and 916 said points located on the proximal end of the unrolled sleeve. Consequently, when sleeve 908 is rolled-up as shown in FIG. 16, points 914 and 916 are rolled into the center of the nautilus-shaped lip of sleeve 908 while unroll control lines 904a and 904b are rolled-up alongside the sleeve.

In contrast, roll-up control lines 902a and 902b are attached to the cannula at points 918 and 920, respectively. Both points 918 and 920 are located on arc 910. When the sleeve is rolled-up, as shown in FIG. 16, the roll-up control lines 902a and 902b run from their respective points of attachment 918 and 920, along the exposed side of the rolled-up sleeve, and enter the control lumens 922 and 924 at points 926 and 928 respectively. After entering the control lumens, the roll-up lines proceed through the control lumens until exiting at points (not shown) proximally located on the cannula.

FIG. 17 shows the same arterial balloon catheter and associated filter as FIG. 16 but with the sleeve 908 fully unrolled and capturing filter 906. The unrolled sleeve provides a compact, smooth profile for the device's introduction to and retraction from a vessel. In order to unroll the sleeve from the FIG. 16 position, the unroll lines 904a and 904b of FIG. 17 have been pulled in a proximal direction, away from the cannula tip. Consequently, points 914 and 916 are positioned at the proximal end of unrolled sleeve 908.

When the sleeve is in the unrolled state, the roll-up control lines 902a and 902b run from points 918 and 920 respectively, along the underside of the sleeve 908, around the proximal end of the sleeve, and then distally along the outer side of the sleeve before entering the control lumens 922 and 924 at points 926 and 928 respectively. After entering at points 926 and 928, the roll-up control lines 902a and 902b travel through the control lumens until exiting the control lumens at points (not shown) located at the proximal region of the cannula. When the sleeve is in the unrolled position as shown in FIG. 17, the roll-up lines may be pulled in a proximal direction, away from the cannula tip. Pulling the roll-up lines causes sleeve 908 to roll-up until reaching the rolled-up state shown in FIG. 16. In a preferred method of use, the sleeve 908 is unrolled prior to insertion of the cannula in a vessel, rolled up during mesh deployment and once again unrolled prior to cannula retraction.

Figure 18:
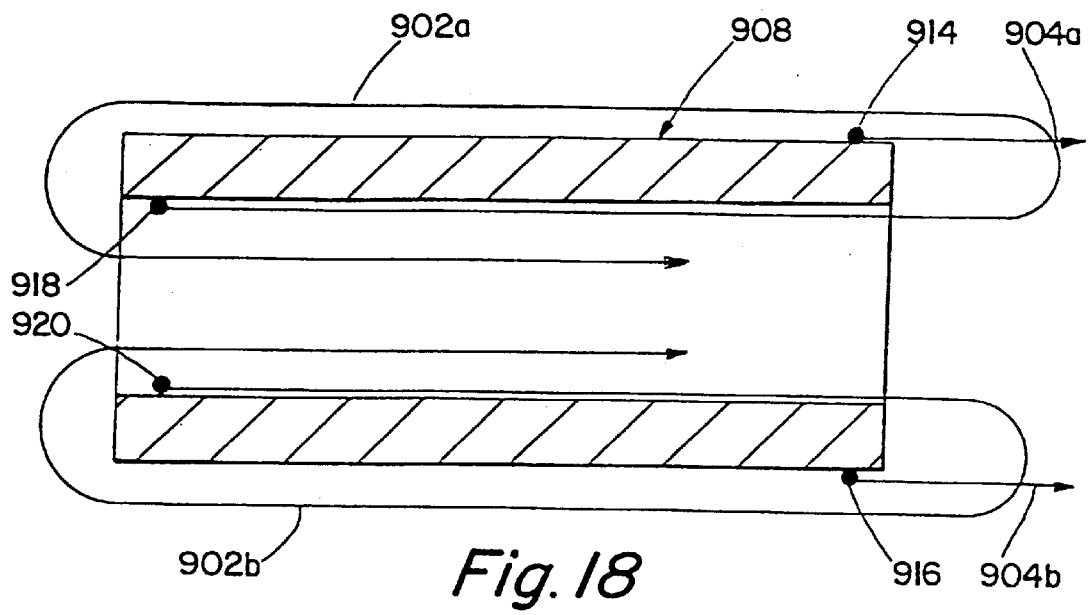
FIG. 18 shows detail of an unrolled filter sleeve and accompanying control lines.

FIG. 18 shows a cross-sectional detail of the sleeve 908 in the unrolled state, with emphasis on the points of attachment for the control lines. In the FIG. 18 embodiment, the sleeve, which is a continuous about 360 degrees (not shown), is directly connected to the two roll-up lines 902a and 902b at points 918 and 920 respectively. Alternatively, the roll-up lines are attached directly to the cannula at points neighboring 918 and 920 located immediately distal to the distal end of the sleeve. Pulling the roll-up lines 902a and 902b in a proximal direction, as shown by the arrows in FIG. 18, causes the sleeve to roll-up like a condom. Accordingly, the sleeve material should be thin enough to avoid bunching and to provide smooth rolling in reaction to the proximal force exerted by the roll-up lines. In a preferred embodiment, the sleeve is made of latex, with a thickness of between 3 and 14 thousandths of an inch. In a more preferred embodiment, the sleeve is made of latex with a thickness of between 4 and 16 thousandths of an inch. The invention may also use silicone or another silastic, biocompatible material to construct the sleeve. Other materials as are known in the art may permit use of a sleeve with less than 4 thousandths of an inch provided the material gives suitable assurances against breaking or tearing.

Figure 19:
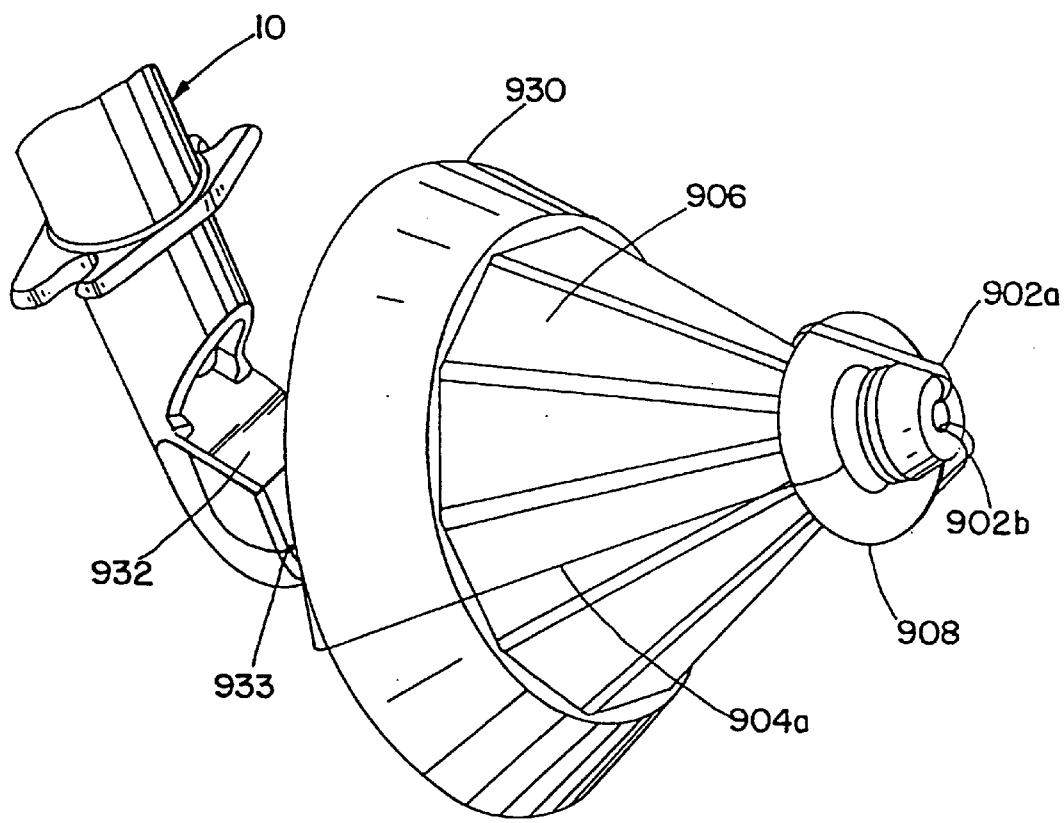
FIG. 19 is a three-dimensional drawing of a balloon aortic cannula with a filter sleeve in the rolled up position.
Figure 19A:
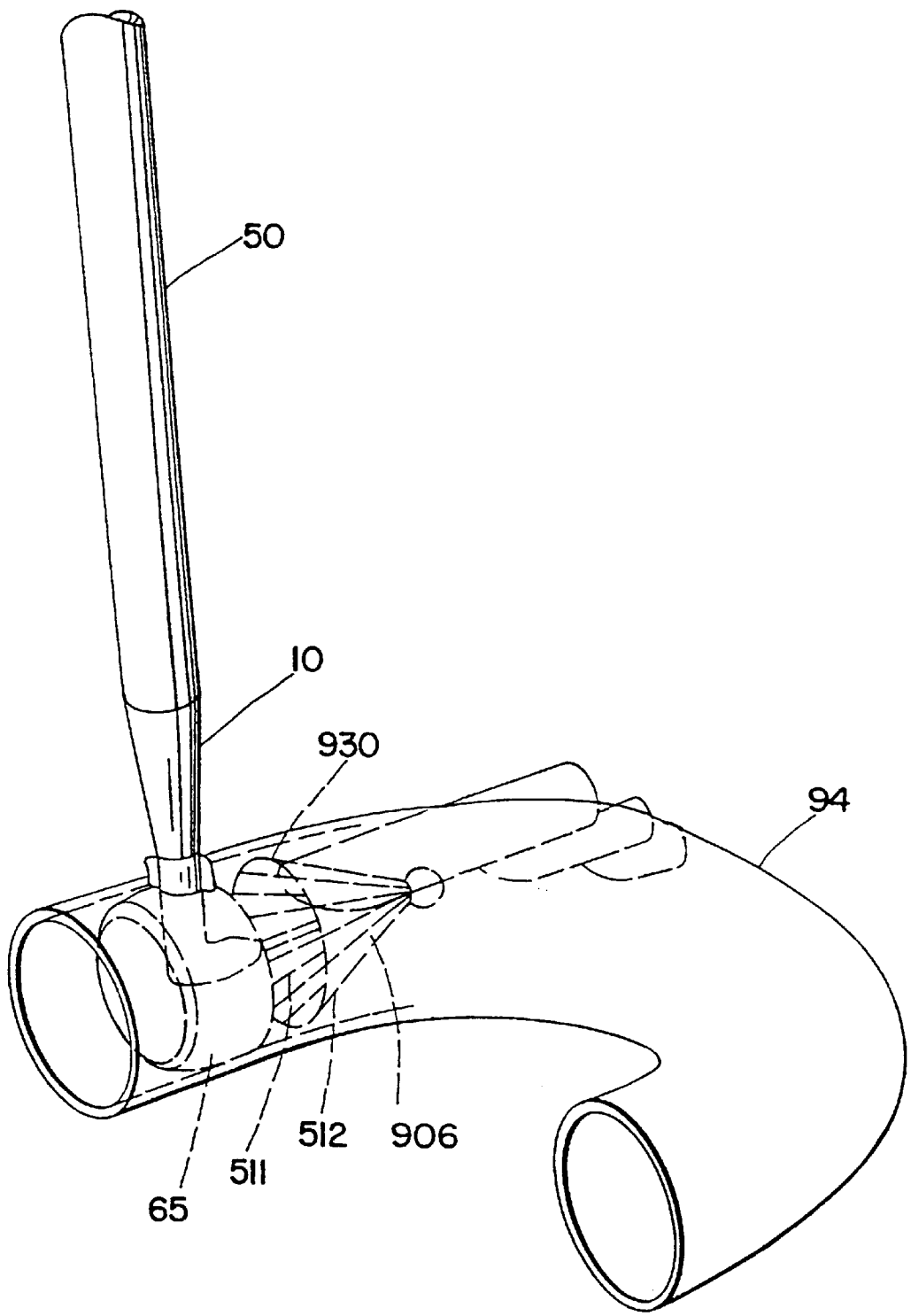
FIG. 19A shows the cannula of FIG. 19 in use.

FIG. 19 is a three-dimensional depiction of the cannula 10, filter 906 and sleeve 908, with sleeve 908 in the rolled-up state. In one embodiment the filter 906 is located distal to the cannula opening such that cannula output is filtered upon leaving the cannula. In another embodiment, the filter is located proximal to the cannula opening such that cannula output is downstream of the filter. The cannula opening may optionally have a planar diffuser 932. Filter 906 is made of mesh which is contiguous with a sealing skirt 930. With the exception of entrance point 933, both the roll-up and unroll lines enter and exit the cannula at points not shown. In a preferred embodiment, the control lines attach to a control line actuating mechanism such as a capstan, ring or pulley (also not shown). In this embodiment, the structure adapted to open and close the filter may be an umbrella frame (not shown), such as depicted in FIG. 10, or alternatively an inflation balloon (not shown), such as shown in FIG. 7 and FIG. 9. The FIG. 19 embodiment may be used with any of the various means to actuate the structure as described herein. Pulling the unroll control lines 904a and 904b in a proximal direction causes the capture sleeve to roll out over the top of the filter. Subsequently pulling the roll-up control lines 902a and 902b rolls-up the captured sleeve thereby permitting filter deployment. In FIG. 19 the unroll lines are oriented at an angle of 180 degrees from one another along the circumference of the filter (thus 904b is not shown). The roll-up lines 902a and 902b are similarly oriented at an angle of 180 degrees from one another. However, as with the inventions of FIGS. 16–18, this embodiment may employ any number of control lines spaced at varying distances around the outer diameter of the filter sleeve. Cannula 10 is shown in use in FIG. 19A. Balloon occluder 65 expands to engage the lumen of aorta 99. FIG. 19A also shows an expansion frame comprising an umbrella having a plurality of primary struts 511 and a plurality of secondary struts 512 which are connected to the primary struts at about the midpoint of the primary struts.

Figure 20:
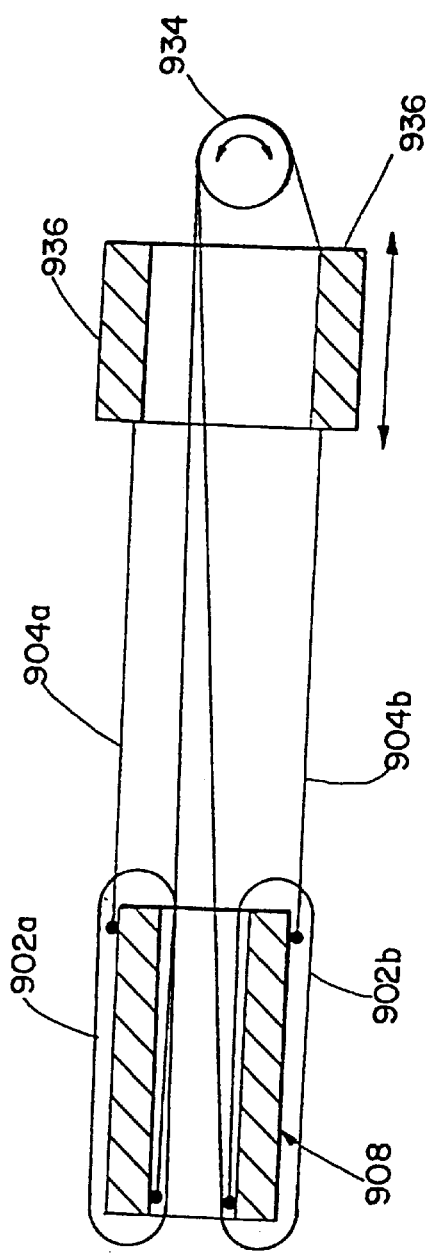
FIG. 20 is a longitudinal view of a balloon aortic cannula including a sleeve deployable by virtue of a pulley mechanism.

FIG. 20 shows an alternative embodiment wherein one control ring 936 controls rolling and unrolling of the sleeve 934 with the assistance of a pulley mechanism. The control ring 936 is movable in both the proximal and distal directions along the outer diameter of the cannula (not shown). Control ring 936 is directly attached to unroll control lines 904a and 904b and attached to roll-up control lines 902a and 902b through pulley 934. Proximal movement of the control ring causes the sleeve 908 to unroll. Distal movement conversely causes sleeve 908 to roll up.

Figure 21:
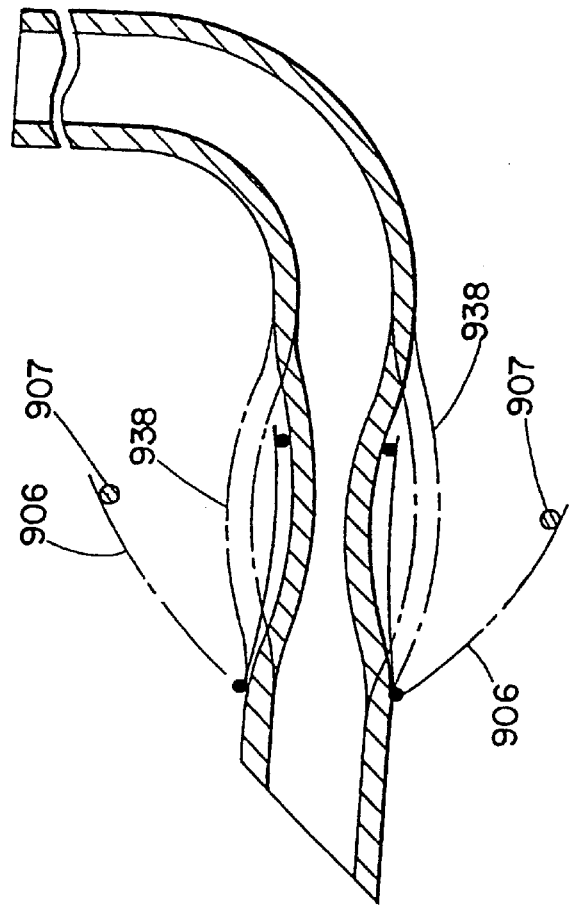
FIG. 21 is a longitudinal view of a balloon aortic cannula wherein the cannula has a collapsible section which can accommodate the lip of the filter.

In another embodiment of an arterial balloon cannula, shown in FIG. 21, the cannula contains a collapsible section such that it can accommodate the filter seal 907 and the filter 906 and any other components of the filtration means. The collapsible section 938 is made out of an elastomeric material, such as latex. In another embodiment the collapsible section is a double walled balloon. In a preferred embodiment the section is made of a flexible material with built in memory such that the collapsible walls automatically return to their non-collapsed state when deployment force expands the filter. The collapsing section 938 begins just proximal to the site of the filter seal 907 when the filter is in the collapsed state. In the embodiment shown, the collapsing section has a length equal to the length of the filter 906 and filter seal 907. In an alternative embodiment, the collapsing section extends to the tip of the catheter from just proximal to the filter seal. The deformable section collapses radially inward when the filtration assembly is closed in order to produce a low-profile distal end to the cannula. Thus, a portion of the radial volume of the cannula is occupied by the filtration assembly when the filtration assembly is deployed; however, the blood flowing through the cannula subsequently blows the deformable cannula walls outwards to allow the flow of blood through the entire cannula diameter. It is to be understood this embodiment may be used in combination with the sleeve embodiments previously shown herein.

In another embodiment of an arterial balloon cannula, with associated filter shown in FIGS. 22 and 23, the blood cannula 10 is composed of a medically acceptable elastic material, such as latex, silicone, rubber, and the like. As shown in FIG. 23, the blood cannula has an intrinsic length and diameter which characterizes the cannula when it is not under axial stress. The intrinsic length and diameter of the cannula varies according to vessel size. The cannula may be closed with a cap diffuser of the type disclosed in FIG. 12. Alternatively, the cannula may be only partially closed at the tip as in FIG. 13. As shown in FIG. 22, a stylet 944 is placed in the cannula 10 and engages the cannula tip. In an alternative embodiment, the stylet engages a ring suspended at the opening of an open tip. When inserted fully into the cannula, the lengthy stylet 944 engages the distal tip of the elastic cannula and axially stretches the cannula body. In this way the cannula is stretched so as to reduce cannula diameter upon introduction into the vessel. A finger grip 946 secured to the proximal end of the stylet includes latch member 948. The latch member engages a recess 950, formed on a proximal fitting 952 of the cannula, in order to maintain the cannula's stretched configuration. After insertion in the vessel, the elastic cannula is radially expanded and shortened by depressing latch member 948 and withdrawing the stylet as in FIG. 23.

In this embodiment, the filter 908 is fixed to the outer diameter of the unexpanded elastic cannula by tether lines 954 and 956 such that, when the stylet is introduced, cannula expansion causes the tether lines to go taut, which in turn contours the filter to the cannula. Consequently, as shown in FIG. 23, when the stylet is withdrawn, the cannula shortens thereby permitting expansion of the filter. Although various biasing and filter opening mechanisms may be used, in one preferred embodiment, the filter itself is made of memory-wire biased to an open state.

Figure 24:
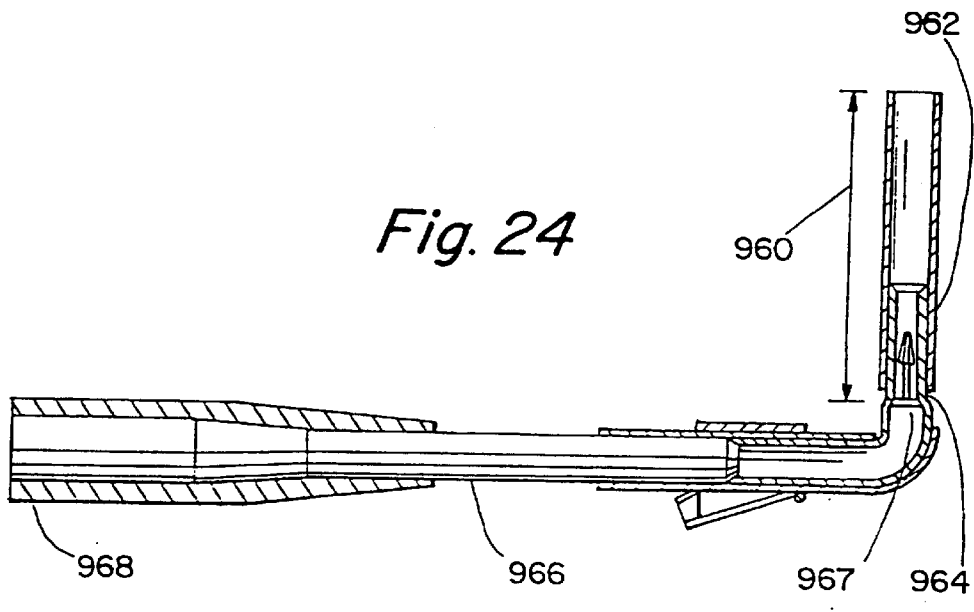
FIG. 24 is a longitudinal view of a cannula wherein the expander is proximal to the collapsible portion of the distal cannula.
Figure 25:
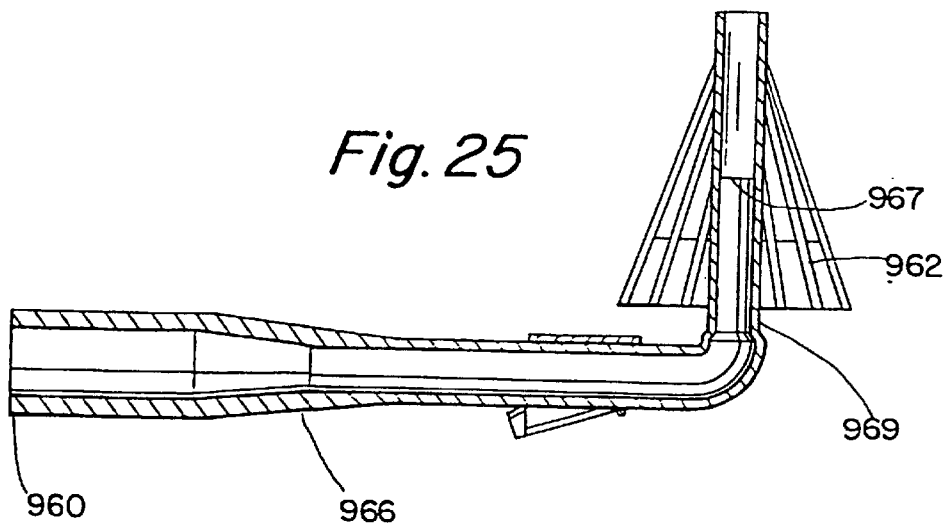
FIG. 25 is a longitudinal view of a cannula wherein the expander has been inserted into the collapsible portion of the distal cannula.

In another embodiment shown in FIGS. 24 and 25, the distal cannula portion 960 upon which the filter assembly 962 is mounted is, at least in part, a radially flexible material or composite construction which is normally in a necked down, contracted position. This allows the contracted filter assembly 962 to create as small of a profile as possible for insertion into the blood vessel. The necked-down portion 964 of the distal cannula is opened by inserting a close fitting expander 966 through the necked-down portion. The expander 966 has a distal end 967. As a result of the expander insertion, the filter assembly 962 exhibits an extruding profile relative to the outer contours of the distal cannula. Optionally as shown in FIG. 24, the filter assembly 962 may be fully deployed by a deployment mechanism (not shown), as previously described herein. In both FIGS. 24 and 25, the expander is fixed relative to the proximal cannula 968. Both are moved distally relative to the distal cannula so as to insert the expander into the collapsible section. Alternatively, the expander 966 may move independent of the proximal cannula 968.

In another embodiment shown is FIGS. 26 and 26A to 26D, cannula 350 includes filter 906 having skirt 970 disposed around its outermost edge. Skirt 970 is an elastomeric strip of material (e.g., silicon or other suitable material) attached to the proximal edge of the filter mesh. Skirt 970 forms a compliant edge which conforms to vessel lumen topography and gives a better seal with the vessel lumen when the filter is deployed. Moreover, the compliant edge 970 allows for changes in the vessel interior dimension as the vessel pulses from systole to diastole. Both unroll control lines 904a and 904b, as well as roll-up control lines 902a and 902b (not shown) are routed through tube 978 and then through the cannula housing at location 971 and thereafter ride within tubing 972 to the point where they are manipulated outside of the body. In addition to the roll-up and unroll control lines, a fifth control line is also carried through tube 972 and location 971 for the purpose of operating the umbrella frame 973 depicted in FIG. 26. This control line can ride either inside or outside of tube 978. The umbrella frame consists of a series of primary struts 974 extending from the distal to proximal end of the mesh and disposed circumferentially thereabout, and a series of secondary struts 975. Struts 975 connect at their proximal end to struts 974 and at their distal end are slidably connected to the axis of the conical filtration mesh. Secondary struts 975 therefore operate to open and close the expansion frame between a radially expanded and radially contracted condition.

In another embodiment shown in FIG. 27, cannula 350 includes on its distal end a "windsock" or open-ended sleeve 976 which is either a porous mesh, a non-porous material (e.g., silicon), or a non-porous material with holes which allow some degree of lateral blood flow. In FIG. 27, the windsock cannula is shown deployed within aorta 99. As can be seen, embolic debris dislodged upstream of the cannula will be carried through the windsock 976 and will exit the distal opening 977. Sleeve 976 thereby prevents passage of embolic material laterally in the region of the carotid arteries and thereby prevents or reduces the occurrence of embolic material reaching the brain. At the same time, however, the windsock apparatus overcomes difficulties associated with filter blockage due to blood clotting and buildup of debris by delivering a high volume of blood downstream of the carotid arteries without the need to pass laterally through the sleeve.

It is to be understood that the cannula devices of FIG. 16–FIG. 27 may optionally employ a balloon occluder proximal to the filter, as disclosed in FIG. 1–FIG. 10.

Figure 28:
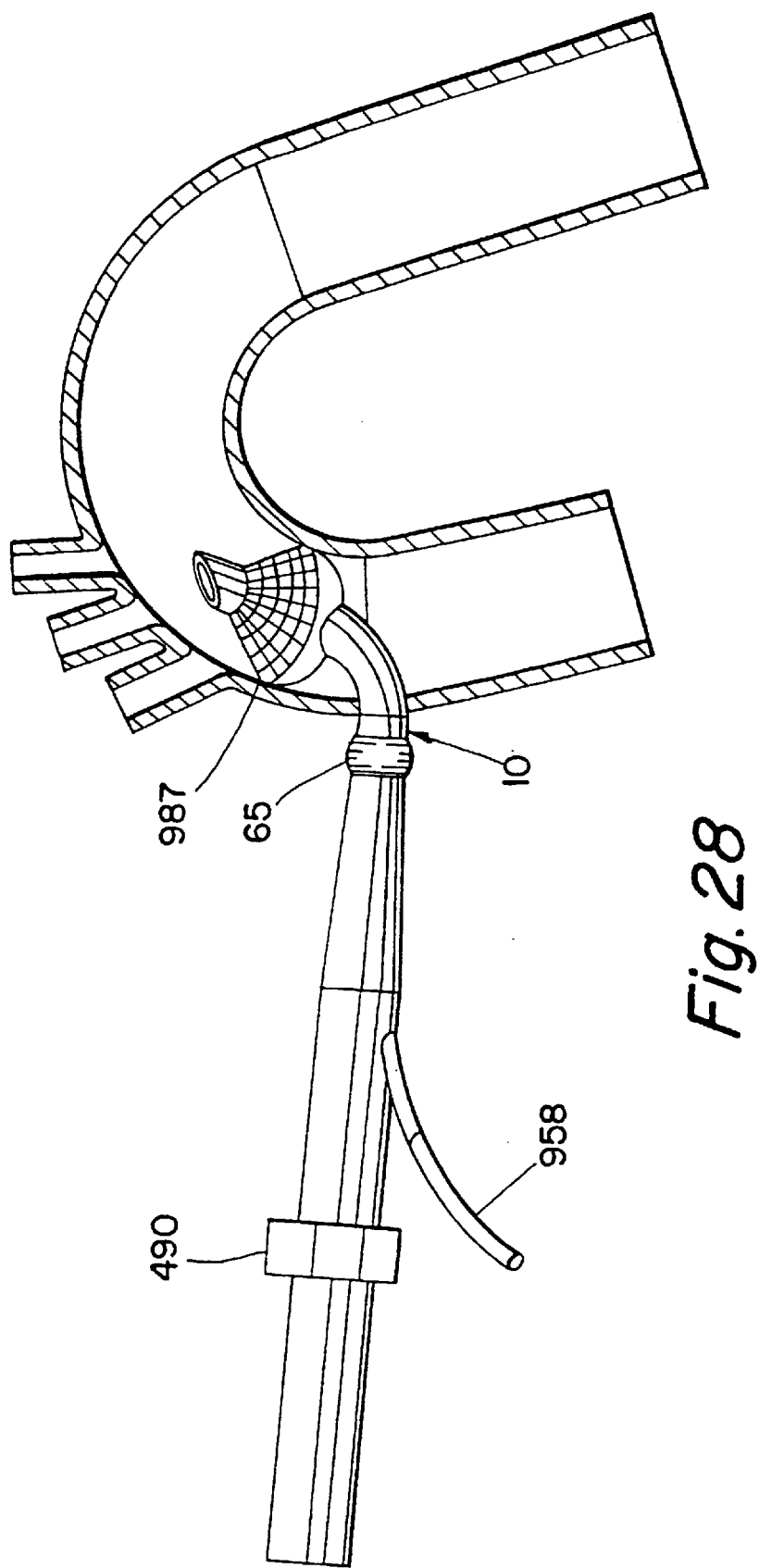
FIG. 28 is a longitudinal view of a balloon aortic cannula wherein the filter and balloon are of integrated construction.

In another embodiment of an arterial balloon cannula, as shown in FIG. 28, a filter and balloon occluder are integrated as one piece 987 and disposed concentrically about the cannula, 10. As a result, the cannula employs a single inflation port 988 for both occlusion of the vessel and deployment of the filter. In a preferred embodiment, a slide 990 is used to collapse the filter-balloon unit via control lines (not shown) when passage of the device through the vessel is required.

Figure 29:
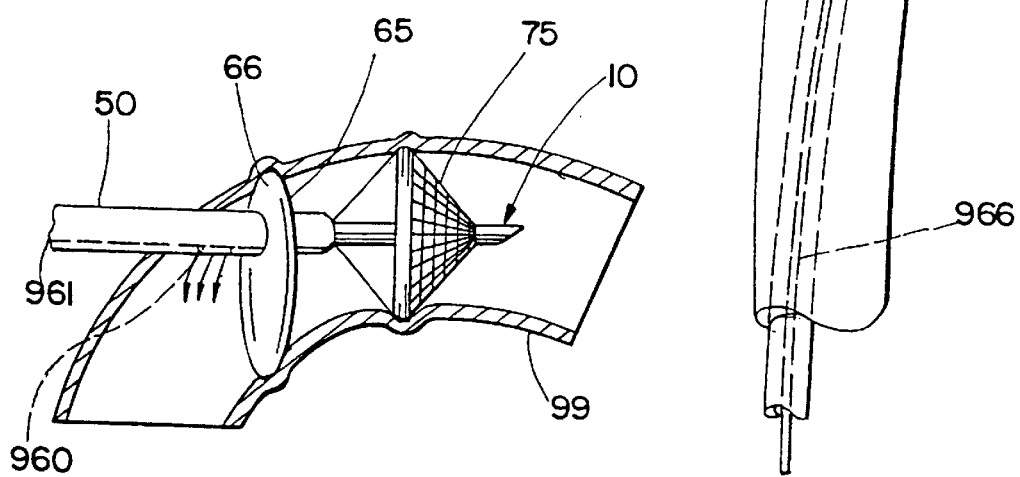
FIG. 29 is a longitudinal view of a balloon aortic cannula wherein the balloon occluder contains a conduit for delivery of solutions to the heart side of the occluder.

In another embodiment of an arterial balloon cannula, as shown in FIG. 29, a cannula contains an opening 992 proximal to the balloon occluder 65 and filter 75. The opening is linked by a conduit 991 which runs along the inside of the cannula and is isolated from the cannula blood flow. In a preferred embodiment the conduit carries a source of myocardial prevention solution, such as a cardioplegia solution, which is pumped into the heart side of the balloon-occluded aorta. Alternatively, the conduit may pump saline solution or a solution which facilitates pressure monitoring via the conduit. The construction and operation of the valve system to accommodate cardioplegia output on a perfusion cannula is explained in detail in Hill, U.S. Pat. Nos. 5,522,838, 5,330,498 (see FIG. 6), and 5,499,996, incorporated herein by reference.

Figure 30:
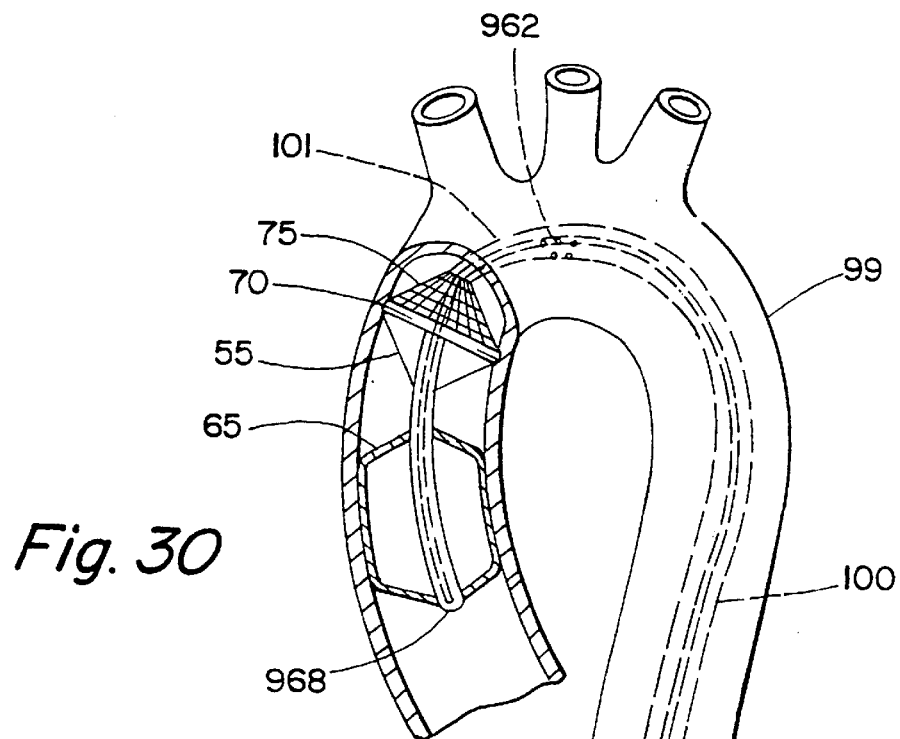
FIG. 30 is a longitudinal view of a catheter as in FIG. 11 wherein the catheter contains openings and lumens for delivery of solutions to the heart side of the balloon occluder.

In an arterial balloon catheter embodiment, as shown in FIG. 30, a catheter similar to the catheter in FIG. 12 includes openings 992 located proximal to the balloon so as to deliver oxygenated blood to the arterial side of the balloon occluder. Additionally, the arterial balloon catheter contains a fluid-isolated second lumen 996 and opening 998 at the distal end of the catheter 100 for delivery of cardioplegia solutions to the heart side of the balloon occluder 65.

Figure 31:
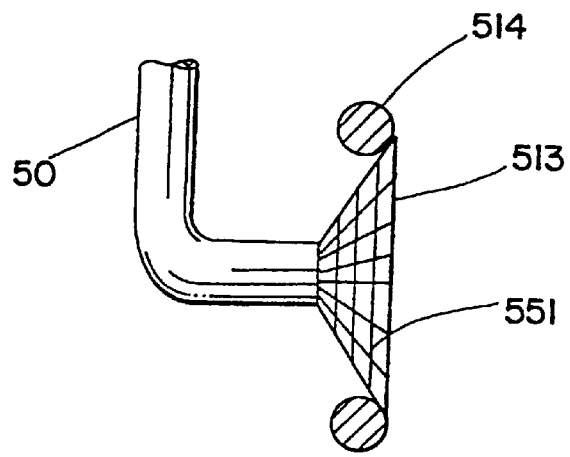
FIG. 31 is a longitudinal view of a cannula with blocking dam.

In another embodiment, a device for occluding arterial vessels is provided by a cannula having a dam or other impermeable structure as shown in FIG. 31. Cannula 50 is equipped with mechanical dam structure 513 at the distal end of the cannula, dam 513 having a plurality of lifting arms 551. The dam may optionally include a balloon seal 514 disposed circumferentially and continuously about 513. Balloon 514 may be filled with saline, self-expanding foam, or a combination of both. Dam 513 is constructed of any nonpermeable material, examples of which include silicon, urethan, or other occlusive barriers.

Figure 32:
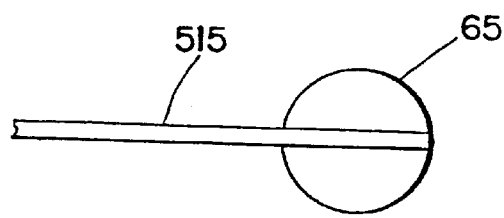
FIGS. 32 and 32A are longitudinal views of a balloon occluder on catheter.
Figure 32A:
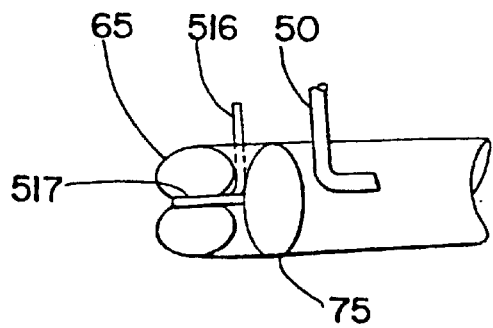

A balloon occluder on a catheter in accordance with another embodiment is depicted in FIGS. 32 and 32A. Referring to FIG. 32, catheter 515 includes balloon occluder 65 disposed about the distal region thereof. The catheter may be used as a standalone device or with a blood cannula. Cannula 515 includes an inflation lumen for inflating balloon 65, and may optionally include a second lumen for delivery of fluids, such as cardioplegic solution. In use, the device is deployed as shown in FIG. 32A. Catheter 515 may be deployed through cannula 50 and enter the aorta upstream of cannula 50. Catheter 515 may optionally further include filter 75. In another embodiment, catheter 515 is delivered through cardioplegic cannula 516. In this embodiment, catheter 515 includes second inner lumen 517 for delivery of cardioplegia solution to the heart. Thus, the occlusion catheter can be delivered either through an additional lumen on perfusion cannula 50 or through an entirely separate cardioplegic cannula 516 which is inserted through the aorta upstream of the entry point 450.

Figure 33:
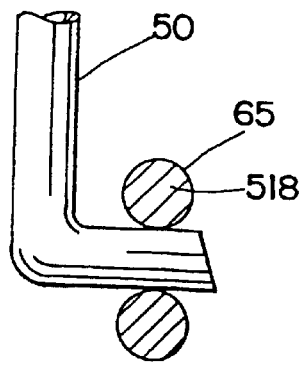
FIGS. 33 and 33A are longitudinal views of a cannula with self-expanding balloon.
Figure 33A:
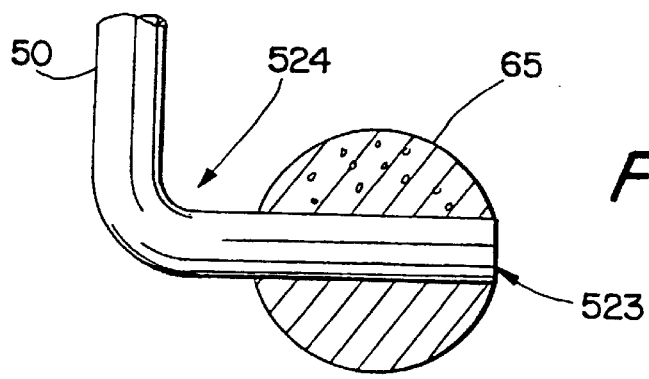

A cannula with a self-inflating balloon is shown in FIGS. 33 and 33A. Cannula 50 includes balloon occluder 65 disposed about a distal region thereof. The balloon is loaded with foam which is biased to expand radially outwardly. Vacuum is applied to the balloon inflation lumen to radially collapse the balloon occluder 65 and thereby compress foam 518. When the cannula is in place within the aorta, the vacuum is released, and balloon occluder 65 expands radially outwardly. FIG. 33A shows a self-expanding balloon occluder wherein cannula 50 includes rigid section 524 and deformable section 523 which, upon balloon compression, collapses inwardly to economize on the cross-sectional area of the device.

Figure 34:
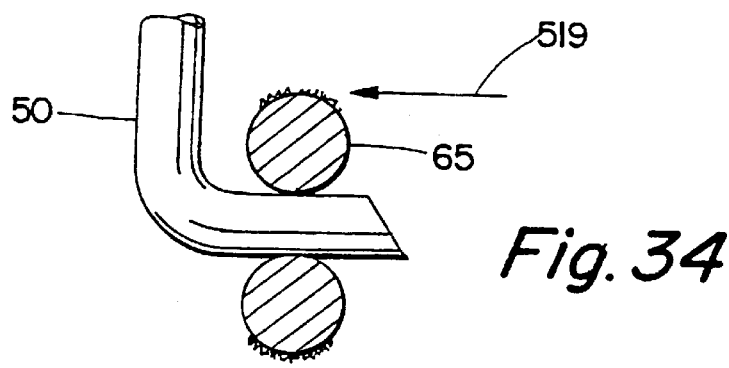
FIG. 34 is a longitudinal view of an adhesive coated balloon cannula.

An adhesive coated balloon cannula is shown in FIG. 34. Cannula 50 includes balloon occluder 65 at a distal region thereof. Balloon 65 is equipped with adhesive coating 519 on an outer radial surface thereof. Adhesive 519 functions to grab and retain any embolic material dislodged from the vessel wall during a procedure.

Figure 35:
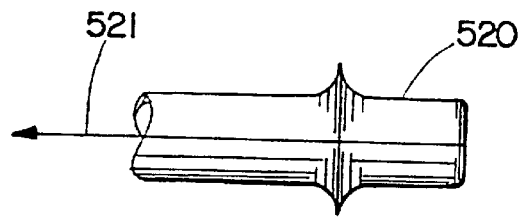
FIGS. 35 and 35A are longitudinal views of an expandable wire occluder.
Figure 35A:
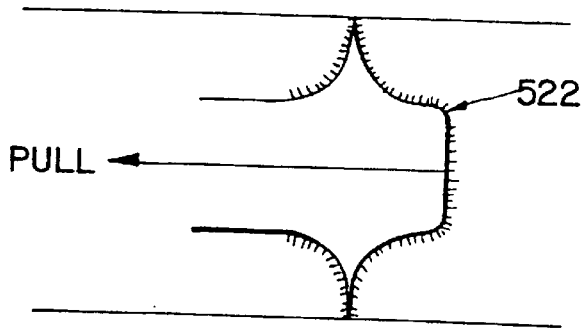

An expandable wire occluder is shown in FIGS. 35 and 35A. Wire 520 is preformed into a shape about the distal end of the cannula so that it will expand radially outwardly when longitudinally compressed. The device further includes pulling member 521 which is connected to the distal end of wire 520. When pulled, member 521 causes expanding wire 520 to expand radially outwardly as shown in FIG. 35A. The expanding wire 520 may optionally be further equipped with an impermeable elastic coating 522.

Figure 36:
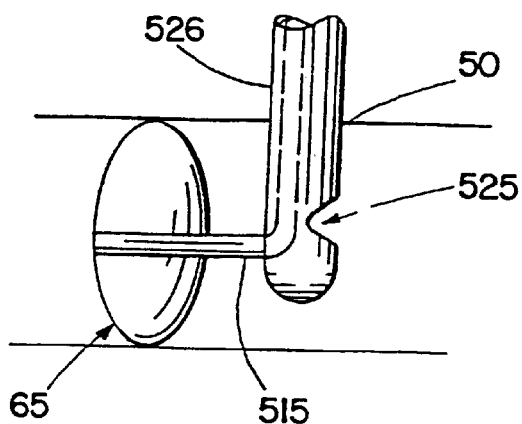
FIG. 36 is a longitudinal view of a cannula introducer.

A cannula introducer is shown in FIG. 36. Cannula 50 includes bypass output port 525 in one radial position, and passage 526 in another radial position, preferably 180° apart. Passage 526 is adapted to receive a balloon catheter 515 having balloon occluder 65 on a distal end thereof. This modular design allows the balloon catheter 515 to be inserted and deployed and retracted independently of the cannula.

Figure 37:
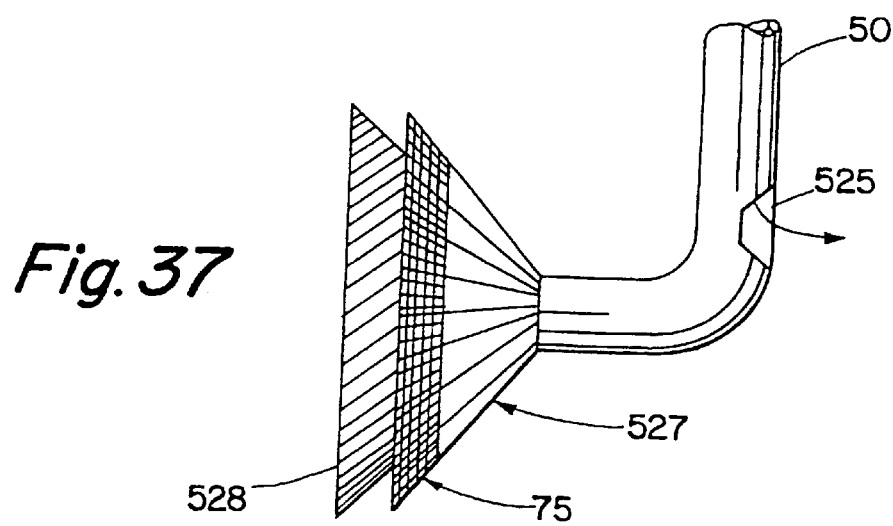
FIG. 37 is a longitudinal view of an integrated occlusion cape.

An integrated occlusion cape cannula is shown in FIG. 37. Cannula 50 includes bypass output port 525 at a first radial position, and occlusion cape 528 at a second radial position, preferably substantially 180° from bypass output port. Also included on the distal end of cannula 50 are mesh 75 and mechanical support structure 527. Mesh filter 75 is preferably equipped with an elastomeric skirt disposed circumferentially about the outer diameter of the mechanical support structure. The support structure is typically outside of mesh 75. Cape 528, once deployed, covers and lines mesh filter 75 thereby blocking passage of fluids. Cape 528, once retracted, is detached and withdrawn into a port in cannula 50 for removal from the aorta. The cape can be inverted to block fluid flow in the opposite direction.

Figure 38:
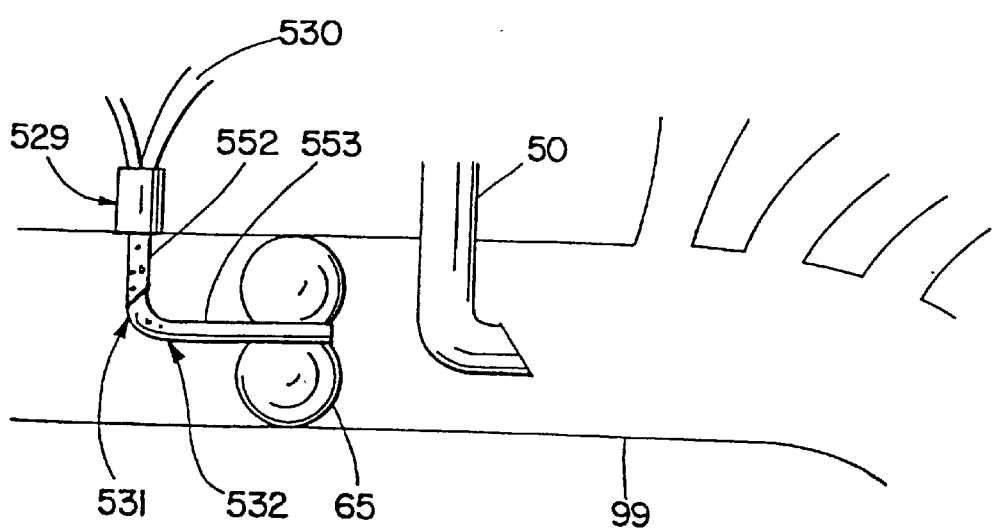
FIG. 38 is a longitudinal view of a cardioplegia occlusion cannula in use.

The use of a balloon occluder catheter in conjunction with a cardioplegic catheter is depicted in FIG. 38. Bypass cannula 50 is inserted downstream of cardioplegic cannula 520. Balloon occluder 65 is disposed on a catheter 553 which is insertable through lumen 530 on cardioplegic cannula 529. Cannula 529 is equipped with cardioplegia solution exit port 531 and optionally having diffuser ports 552. Catheter 553 may optionally include solution ports 532. The advantage of such a system over a cannula-based balloon occluder is that the occluder is independent of the bypass cannula. Therefore, this design is compatible with any bypass cannula design. Moreover, the bypass cannula is available for placement anywhere distal of the occluder.

Figure 39:
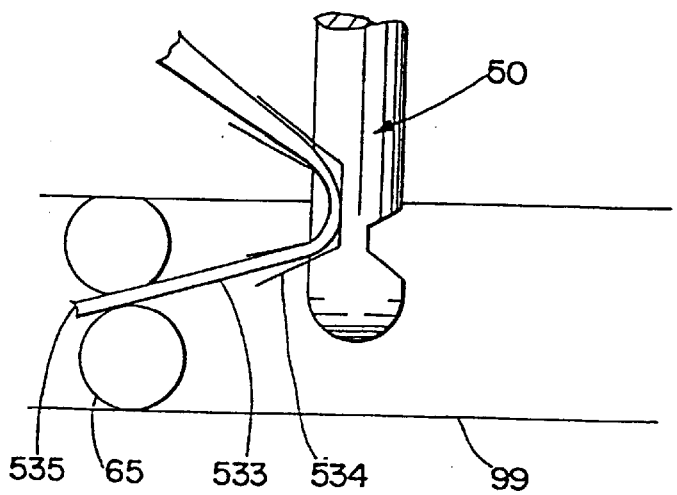
FIG. 39 is a longitudinal view of a cannula with occluder guide.

An aortic occluder with modular design is shown in FIG. 39. Cannula 50 includes occluder guide 534 at a distal end thereof. Guide 534 comprises a lumen adapted to receive balloon occluder device 533. Occluder 533 includes balloon 65 and fluid port 535 as a conduit for cardioplegic solution. Guide 534 is advantageous in that it directs or positions the occluder at a desired location rather than allowing the occluder to randomly position itself.

Figure 40:
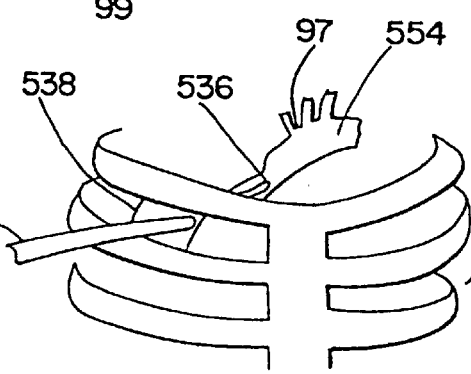
FIG. 40 is a depiction of the sternum and aorta of a patient having an occlusion cannula in use.

Human anatomy including the rib cage with deployed occluder is depicted in FIG. 40. Occluder cannula 50 is disposed through access port 538 and thereafter enters the aorta behind sternum 554. The rib cage is depicted generally by numeral 537. Occluder 536 is shown deployed within aorta 99. The concept of port access allows a surgeon to enter the aorta via a port for a minimally invasive approach. By accessing the aorta directly, the device is deployed without the need for visual guidance, e.g., fluoroscopy, echocardiography. This device would obviate the need for a sternotomy procedure which is generally associated with conventional coronary artery bypass grafting surgery. In use, the aortic occluder passes through the access port to the aorta. Once positioned on the aorta, the occluder device is inserted into the vessel and the occluder is deployed. The occlusion device may comprise a single one-piece occluder cannula or multiple components. One simple design would utilize an inflation balloon on the end of a cannula. The shaft of the cannula could be flexible or stiff depending on whether the surgeon prefers to direct the occluder using a clamp or trocar or prefers a more steerable unit. The cannula may include one or more lumens for inflation and fluid passage.

Figure 41:
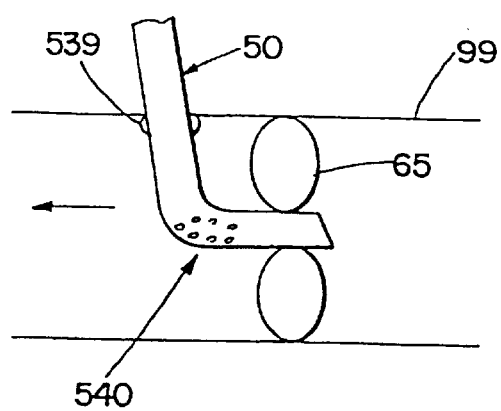
FIG. 41 is a longitudinal view of an L-shaped single-piece occluder.

A single-piece occluder is shown in FIG. 41. Occluder cannula 50 includes occlusion balloon 65 disposed on its distal end. Cannula 50 is equipped with infusion ports 540 for passage of any appropriate fluid, e.g., cardioplegic solution. Cannula 50 optionally includes seating bumps 539 for additional sealing with the interior of the aorta. The L-shaped cannula may be preformed or flexible to allow for self-centering.

Figure 42:
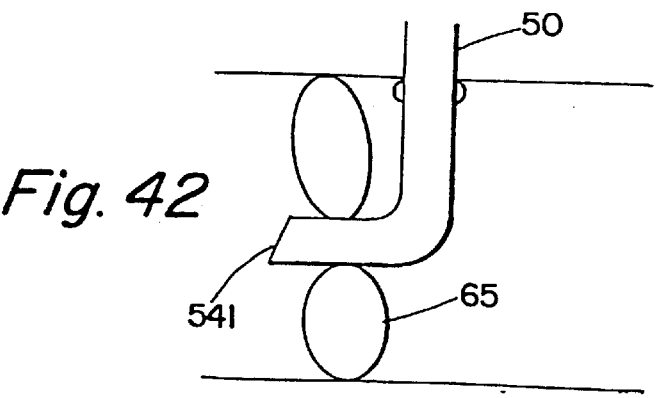
FIG. 42 is a longitudinal view of a J-shaped single-piece occluder.

An alternate design for a single-piece occluder is depicted in FIG. 42. Cannula 50 assumes a J-shape, and includes occlusion balloon 65 on a distal end thereof. Infusion port 541 allows passage of appropriate solution to the heart, e.g., cardioplegic solution. These single component occluders as shown in FIGS. 41 and 42 may be inserted through a pre-slit section of the aorta, or a trocar may be advanced through a lumen, and extended beyond the cannula tip. The trocar would be used to pierce the aorta wall. Once the trocar is in the vessel, the occluder is advanced and then the trocar removed.

Figure 43:
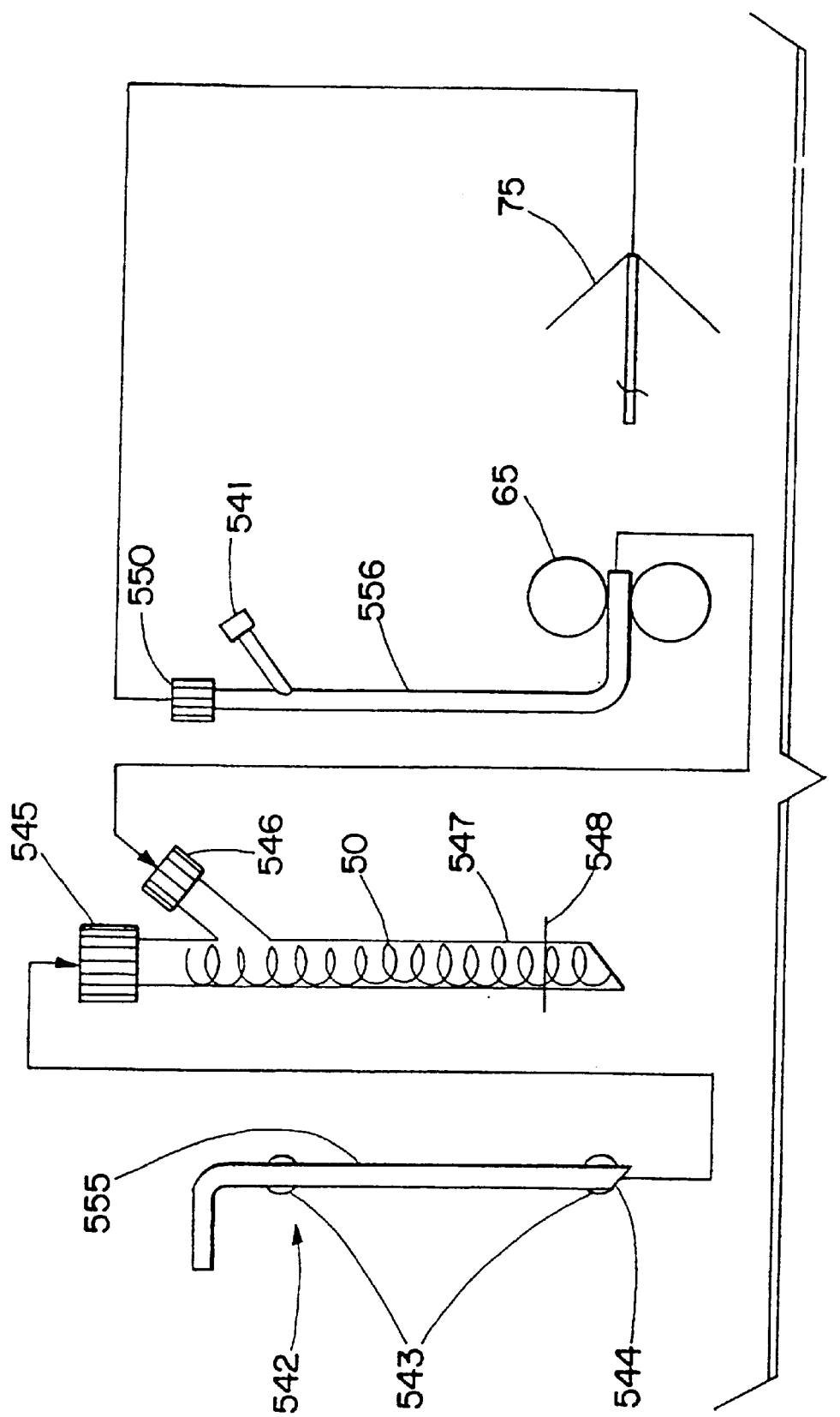
FIG. 43 is a depiction of a multiple component port access aortic occluder.

A multiple component port access aortic occluder is depicted in FIG. 43. The system includes trocar 555 having preshaped configuration 542, sharp tip 544, and position limiters 543. Cannula 50 includes suture plate 548, kink resistant shaft 547, infusion port 545, and hemostasis valve 546. Occlusion catheter 556 includes balloon occluder 565, inflation port 549, and infusion lumen 550. Occluder 556 is shaped to receive filter mesh 75. Cannula 50 is adapted to receive trocar 555 through the infusion port 545, and to receive catheter 556 through hemostasis valve 546. In use, a port access point or window is opened on the patient's chest. Tissue from the port to the aorta is dissected. The trocar and cannula are advanced to the aortic wall. A purse string suture(s) may be required to aid in wound closure and to secure the device. At the desired location, the trocar is advanced through the aortic wall and the cannula is pushed with the trocar. Once in the vessel, the cannula is secured and the trocar is removed. At this point, the occluder (and filter) may be advanced and deployed. Cardioplegia or other fluid may then be circulated through the infusion lumens.

Figure 44:
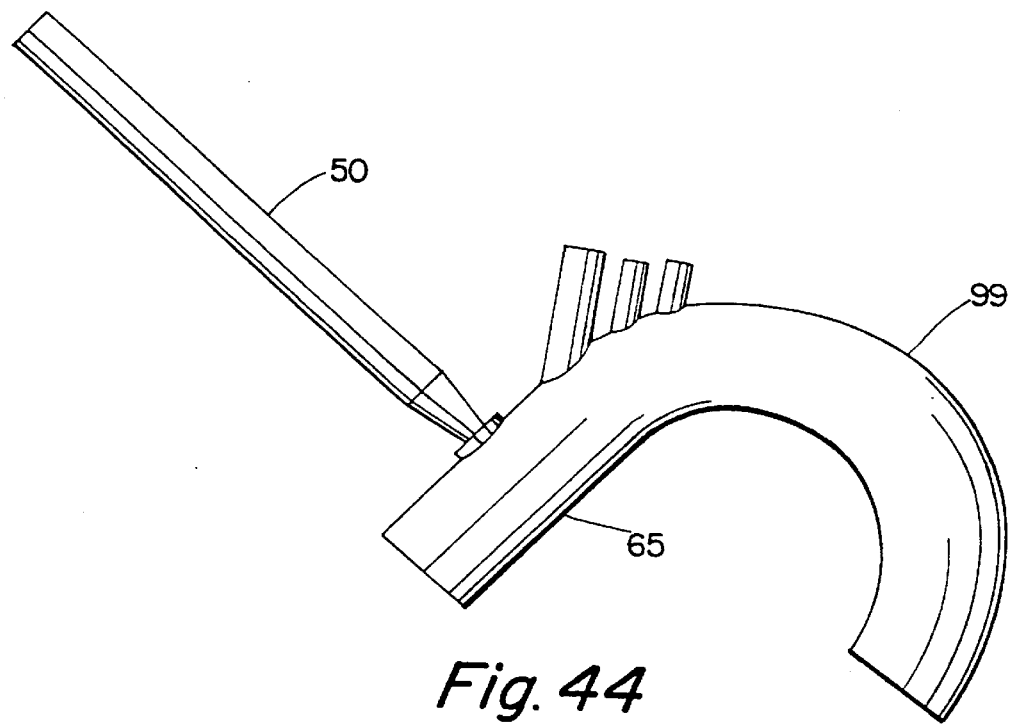
FIG. 44 is a longitudinal view of a balloon aortic cannula in use.
Figure 45:
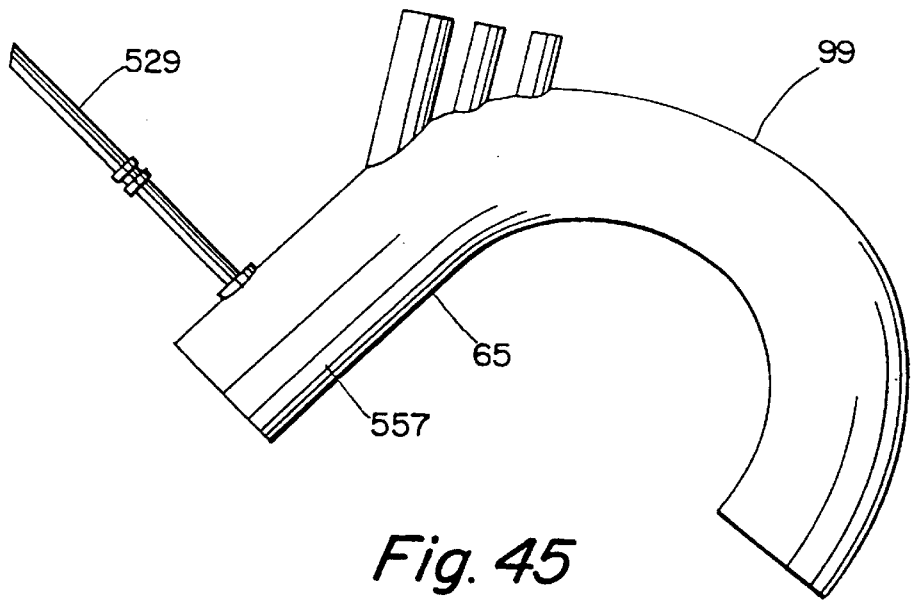
FIG. 45 is a longitudinal view of a cardioplegia cannula and balloon catheter in use.
Figure 46:
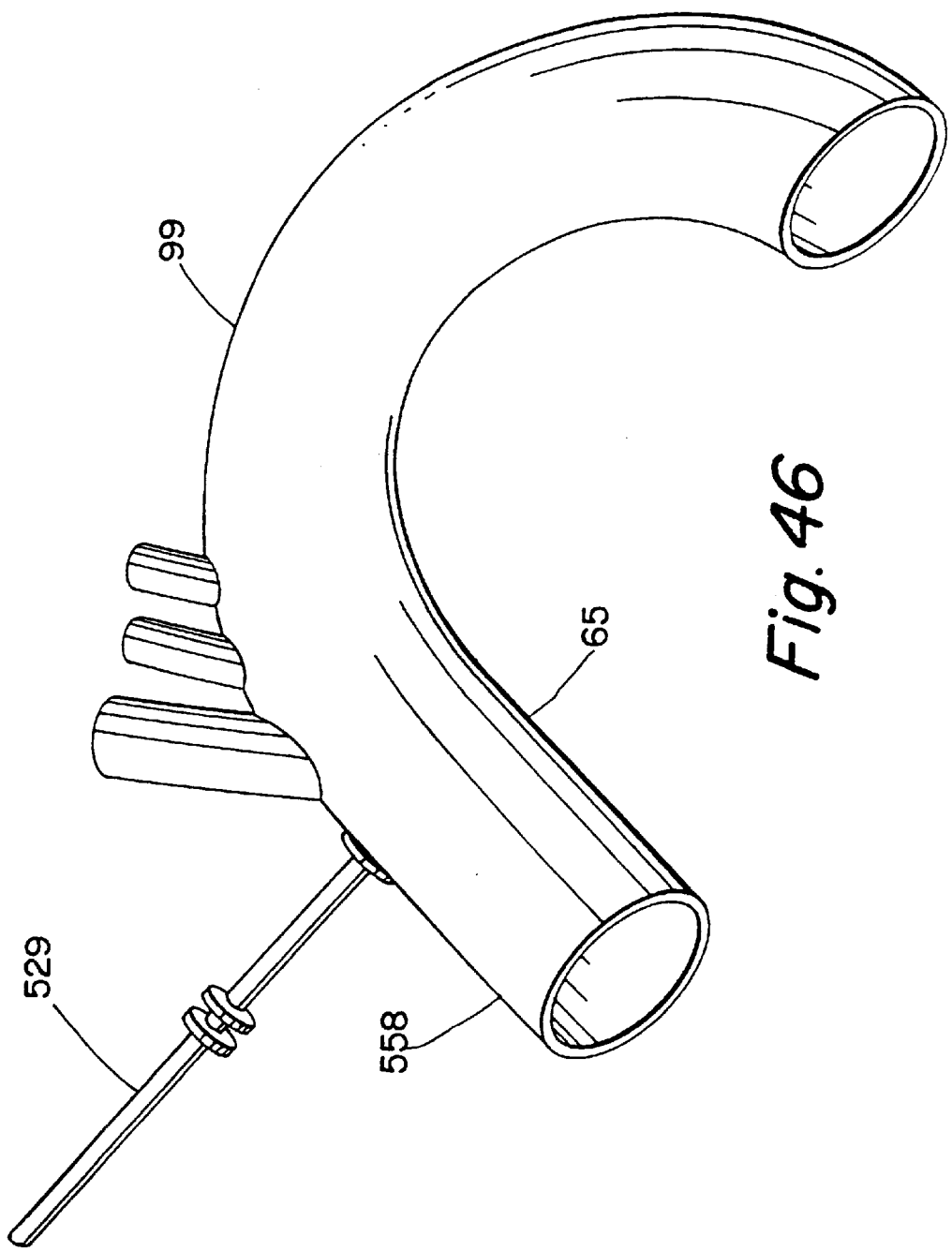
FIG. 46 is a longitudinal view of a cardioplegia balloon cannula in use.

An aortic balloon cannula is depicted in FIG. 44. Cannula 50 is inserted through aorta 99 and includes balloon 65 inflated to occlude the flow of blood in the aorta. The lumen of bypass cannula 50 releases oxygenated blood downstream of occluder 65. In another embodiment, a balloon catheter is used for occlusion as shown in FIG. 45. Cardioplegia cannula 529 penetrates aorta 99 and allows deployment of balloon catheter 557 through cannula 529. Catheter 557 includes occlusion balloon 65 on a distal region thereof. Catheter 557 is deployed through a lumen of cardioplegia cannula 529, wherein the lumen is optionally the same or a different lumen than the lumen which carries cardioplegia solution. In another embodiment, a cardioplegia balloon cannula is provided as depicted in FIG. 46. Cannula 529 includes balloon 65 mounted on a distal region thereof which is expandable within aorta 99 to occlude blood flow therein. Cannula 529 further includes distal port 558 for delivery of cardioplegia solution to the heart.

In use, the arterial balloon catheter is deployed through the femoral artery while maintaining peripheral cardiopulmonary bypass as described in Peters, U.S. Pat. No. 5,433,700, Machold et al., U.S. Pat. No. 5,458,574, Stevens, International Application No. PCT/US93/12323, and Steven et al., International Application No. PCT/US94/12986. Thus, the catheters of FIG. 12 and FIG. 30 may be used to induce cardioplegic arrest of a heart by the steps of maintaining systemic circulation with peripheral cardiopulmonary bypass, occluding the ascending aorta through percutaneous use of the arterial balloon catheter, introducing a cardioplegic agent into the coronary circulation, and venting the left side of the heart as discussed in the above-identified patents and applications. Moreover, the arterial balloon catheter can be used during open heart surgery or for any of a number of other procedures known in the art which involve the heart, aorta, or vasculature. Peripheral cardiopulmonary bypass is connected to a major vein, e.g., the femoral vein to withdraw blood, remove carbon dioxide, oxygenate the withdrawn blood, and return the oxygenated blood to the patient's arterial system through a major artery, e.g., the femoral artery. The catheters of FIG. 12 and FIG. 30 may be introduced by subclavian delivery and induce cardioplegic arrest of the heart as disclosed in Sweezer, U.S. Pat. No. 5,478,309, herein incorporated by reference.

As a purely illustrative example of one of the methods of filtering blood as disclosed herein, the method will be described in the context of cardiac bypass surgery as described in *Manual of Cardiac Surgery*, 2d. Ed., by Bradley J. Harlan, Albert Sparr, Frederick Harwin, which is incorporated herein by reference in its entirety.

A preferred method of the present invention may be used to protect a patient from embolization during cardiac surgery, particularly cardiac bypass surgery. This method includes the following steps: introducing a mesh into an aorta of the patient; positioning the mesh to cover substantially all of the cross-sectional area of the aorta so that the mesh may capture embolic matter or foreign matter in the blood; adjusting the mesh to maintain its position covering substantially all of the cross-sectional area of the aorta; and removing the mesh and the captured foreign matter from the aorta. A variant comprises placing a cylindric mesh at the level of the take off of the cerebral vessel to divert emboli otherwise destined for the brain to other parts of the body.

During the cardiac surgery, the aorta is either clamped a number of times or occluded with a balloon occluder as disclosed herein. Because balloon occlusion and/or clamping the aorta dislodges atheromatous material from the walls of the aorta, which is released into the bloodstream, the mesh must be positioned within the aorta before clamping or balloon occlusion begins. Atheromatous material also accumulates behind the balloon occluder and/or clamps during the surgery and, because removal of the clamps and/or deflation of the balloon occluder releases this material into the bloodstream, the mesh must be maintained within the blood stream for about four to ten minutes after deflation of the occluder and/or removal of the clamps. Because the aorta is often a source of much of the atheromatous material that is eventually released into the bloodstream, it is preferable to place the mesh in the aorta between the heart and the carotid arteries. This placement ensures that foreign matter will be captured before it can reach the brain.

For illustration purposes, the method for balloon occlusion and filtering blood will be described in connection with the device depicted in FIGS. 4 and 5. After a patient has been anesthetized and the patient's chest has been opened in preparation for the bypass surgery, the cannula 10, ranging from about 22 to about 25 Fr. O.D. in size, is introduced into an incision made in the aorta. The cannula 10 is sutured to the aortic wall, and the heart is paralyzed. The balloon aortic cannula is stored in a closed position, in which the balloon occluder 65 is deflated and folded in upon itself, and the mesh 75 is closed. The cannula 10 and its associated structures will not interfere with other equipment used in the surgical procedure.

Saline is introduced into the inflation seal 70 through the actuation assembly (not shown) from an extracorporeal reservoir, and the inflation seal gradually assumes an open position in which the balloon 70 is inflated in a donut-shape and the mesh 75 is opened to cover substantially all of the cross-sectional area of the vessel. In the opened position, the mesh is ready to capture foreign matter in the blood flow. By adjusting the amount of saline introduced into the balloon 70, the surgeon may control the amount of inflation and consequently the degree to which the mesh 75 is opened. Saline is then introduced into balloon occluder 65 under pressure through lumen 60, and from an extracorporeal reservoir, and the balloon occluder gradually assumes an open position (see FIG. 5) in which the balloon is opened to cover substantially all of the cross-sectional area of the vessel. In certain embodiments, the surgeon will dissect around the circumference of the aorta, and a cuff will be installed around the area of balloon occlusion to hold the aorta firmly against the balloon occluder. After the balloon aortic cannula has been thus actuated, blood from a bypass machine is introduced into the aorta through the cannula 10.

It will be understood that balloon occlusion is used to block the flow of blood back into the heart. Balloon occlusion may dislodge atheromatous material from the walls of the aorta and releases it into the blood flow. Because balloon occlusion is performed upstream from the filter 75, the atheromatous material will be filtered from the blood by mesh 75. While the aorta is occluded, the surgeon grafts one end of a vein removed from the patient's leg on to the coronary artery. In another embodiment, arterial grafting, such as internal mammary artery grafting, may be employed. After the surgeon checks the blood flow to make sure there is no leakage, the balloon occluder is deflated. Atheromatous material accumulates behind the balloon occluder and, when it is deflated, this material is released into the blood flow, which will be filtered by mesh 75. The flow rate from the bypass machine is kept low to minimize embolization, and the heart is made to beat again.

During surgery, the position of the mesh may require adjustment to maintain its coverage of substantially all of the cross-sectional area of the aorta. To accomplish this, the surgeon occasionally palpates the outside of the aorta gently in order to adjust cannula 10 so that the mesh 75 covers substantially all of the cross-sectional area of the aorta. The surgeon may also adjust the location of cannula 10 within the aorta.

The balloon aortic cannula may also be used in conjunction with TCD visualization techniques. Through this technique, the surgeon may actuate the inflation seal and mesh only when the surgeon expects a flurry of emboli such as during aortic cannulation, inception, and termination of bypass, balloon occlusion, deflation of an occlusive balloon, aortic clamping, and clamp release.

The surgeon then occludes and/or clamps the aorta longitudinally to partially close the aorta, again releasing the atheromatous material to be filtered by the mesh. Holes are punched into the closed off portion of the aorta, and the other end of the vein graft is sewn onto the aorta where the holes have been punched. The balloon occluder is deflated and/or the aortic clamps are removed, again releasing accumulated atheromatous material to be filtered from the blood by the mesh. The surgeon checks the blood flow to make sure there is no leakage. The heart resumes all the pumping, and the bypass machine is turned off, marking the end of the procedure.

The saline is then removed from the balloon occluder and the inflation seal via the actuation assembly, deflating the balloon occluder, inflation seal, and closing the mesh around the captured emboli. Finally, the balloon aortic cannula, along with the captured emboli, are removed from the body. Because the balloon aortic cannula is in place throughout the procedure, any material released during the procedure will be captured by mesh 75.

When the balloon arterial cannula is used in conjunction with other invasive procedures, the dimensions of the device should be adjusted to fit the vessel affected. An appropriate mesh also should be chosen for blood flow in that vessel. In use, the device may be positioned so that it is placed downstream of the portion of the vessel that is affected during the procedure, by occlusion and/or clamping or other step in the procedure. For example, in order to capture emboli material in a leg artery, the cone-shaped filter can be placed such that the cone points toward the foot.

An advantage of the devices and methods of the present invention and the methods for filtering blood described herein is that it is possible to capture foreign matter resulting from the incisions through which the devices are inserted. Another advantage of the devices of the present invention is that the flexibility of the inflatable balloon allows it to conform to possible irregularities in the wall of a vessel.

While particular devices and methods have been described for filtering blood, once this description is known, it will be apparent to those of ordinary skill in the art that other embodiments and alternative steps are also possible without departing from the spirit and scope of the invention. Moreover, it will be apparent that certain features of each embodiment, as well as features disclosed in each reference incorporated herein, can be used in combination with devices illustrated in other embodiments. Accordingly, the above description should be construed as illustrative, and not in a limiting sense, the scope of the invention being defined by the following claims.

What is claimed is:

1. A cannula, comprising:

an elongate tubular member having a proximal end, a distal end, and a lumen therebetween;

a filter separately insertable through the elongate tubular member; and an expandable occluder deployable from the distal region of the cannula.

2. The cannula of claim 1, further comprising a separate channel within the tubular member.

3. The cannula of claim 2, wherein the filter is insertable through the separate channel.

4. The cannula of claim 1, wherein the expandable occluder is a balloon occluder.

5. The cannula of claim 4, wherein the balloon communicates with an inflation lumen connectable to an external fluid source near a proximal end of the inflation lumen.

6. The cannula of claim 1, wherein the cannula is a blood cannula adapted to pass oxygenated blood for cardiopulmonary bypass procedures.

7. The cannula of claim 1, wherein the occluder is mounted on the distal end of the cannula.

8. The cannula of claim 1, wherein the distal end of the cannula is straight.

9. The cannula of claim 1, wherein the distal end of the cannula is curved.

10. The cannula of claim 1, further comprising a windsock that diverts blood flow.

11. A method for cannulation, comprising the steps of:

inserting a distal end of a cannula into a patient;

inserting a filter through a lumen of the cannula into the patient;

deploying the filter; and expanding an occluder associated with the distal end of the cannula.

12. The method of claim 11, wherein the cannula is inserted into a vessel.

13. The method of claim 12, wherein the vessel is an aorta.

14. The method of claim 11, wherein the cannula is inserted into cardiac tissue.

15. The method of claim 11, further comprising the step of making an incision in the patient.

16. The method of claim 11, wherein the occluder is a balloon occluder.

17. The method of claim 11, wherein the step of deploying the filter comprises inflating an inflation seal comprising a toroidal balloon communicating with an inflation lumen.

* * * * *